US010808266B2

(12) United States Patent
Blum et al.

(10) Patent No.: US 10,808,266 B2
(45) Date of Patent: Oct. 20, 2020

(54) PROPIONIBACTERIAL CELL LINES FOR ORGANIC ACID PRODUCTION

(71) Applicant: S&P Ingredient Development, LLC, Saint Louis Park, MN (US)

(72) Inventors: Paul Blum, Monterey, CA (US); Sambasiva Rao Chigurupati, Omaha, NE (US); Derrick Jermaine White, Lincoln, NE (US)

(73) Assignee: S&P Ingredient Development, LLC, Saint Louis Park, MN (US)

( * ) Notice: Subject to any disclaimer, the term of this patent is extended or adjusted under 35 U.S.C. 154(b) by 0 days.

(21) Appl. No.: 16/443,554

(22) Filed: Jun. 17, 2019

(65) Prior Publication Data

US 2019/0382809 A1   Dec. 19, 2019

Related U.S. Application Data

(60) Provisional application No. 62/686,463, filed on Jun. 18, 2018.

(51) Int. Cl.
| | | |
|---|---|---|
| C12P 7/52 | (2006.01) | |
| C07K 14/195 | (2006.01) | |
| C12N 1/20 | (2006.01) | |
| C12R 1/145 | (2006.01) | |
| C12R 1/02 | (2006.01) | |
| C12R 1/225 | (2006.01) | |

(52) U.S. Cl.
CPC ............ *C12P 7/52* (2013.01); *C12R 1/02* (2013.01); *C12R 1/145* (2013.01); *C12R 1/225* (2013.01)

(58) Field of Classification Search
None
See application file for complete search history.

(56) References Cited

U.S. PATENT DOCUMENTS

| | | | |
|---|---|---|---|
| 2011/0151529 A1 | 6/2011 | Yang | |
| 2015/0275242 A1* | 10/2015 | Osterhout | C12N 15/52 568/852 |

FOREIGN PATENT DOCUMENTS

| | | |
|---|---|---|
| EP | 0141642 A1 | 5/1985 |
| WO | WO8504901 A1 | 11/1985 |
| WO | WO2010097362 A1 | 9/2010 |
| WO | WO2012064883 A2 | 5/2012 |
| WO | WO2017055932 A2 | 4/2017 |
| WO | WO2017185018 A1 | 10/2017 |

OTHER PUBLICATIONS

Kizer et al. Appl Environ Microbiol. May 2008;74(10):3229-41 (Year: 2008).*
Prather et al. Curr Opin Biotechnol. Oct. 2008;19(5):468-74. (Year: 2008).*
Duarte et al. AMB Express (2015) 5:13 (Year: 2015).*
Luna-Flores et al. Biotechnol J. Feb. 2017;12(2). Epub Oct. 20, 2016 (Year: 2016).*
Parizzi et al. BMC Genomics 2012, 13:562 (Year: 2012).*
Accession A0A0F3WHB9. Jun. 24, 2015 (Year: 2015).*
Accession Q6AA87. Sep. 13, 2004 (Year: 2004).*
Invitation to Pay Additional Fees in International Application No. PCT/US2019/37520, dated Aug. 30, 2019, 2 pages.
Guan et al., Genome-Shuffling Improves Acid Tolerance of Propionibacterium Acidipropionici and Propionic Acid Production, 2012, Advances in Chemistry Research, vol. 15, p. 143-152.
Woskow, Propionic Acid Production by a Propionic Acid-Tolerant Strain of Propionibacterium acidipropionici in Batch and Semicontinuous Fermentation, Applied and Environmental Microbiology, Oct. 1991, vol. 57, p. 2821-2828.
Zhu et al., Optimization and scale-up of propionic acid production by propionic acid-tolerant Propionibacterium acidipropionici with glycerol as the carbon source, Bioresource Technology, vol. 101, Jun. 2010, p. 8902-8906.
Wang et al., Propionic acid production in glycerol/glucose co-fermentation by *Propionibacterium freudenreichii* subsp. *shermanii*, Bioresource Technology, vol. 137, 2013, p. 116-123.
Zhuge et al., Improved propionic acid production from glycerol with metabolically engineered Propionibacterium iensenii by integrating fed-batch culture with a pH-shift control strategy, Jan. 2014, Bioresource Technology, vol. 152, p. 519-525.
Coral, Propionic acid production by *Propionibacterium* sp. using low-cost carbon sources in submerged ermentation, 2008, Federal University of Parana, 39 pages.
Zhang et al., Effects of carbon dioxide on cell growth and propionic acid production from glycerol and glucose by Propionibacterium acidipropionici, Jan. 2015, Bioresource Technology vol. 175, p. 374-381.
Wang, Metabolic engineering of *Propionibacterium freudenreichii* subsp. *shermanii* for enhanced propionic acid fermentation: Effects of overexpressing three biotin-dependent carboxylases, Feb. 2015, Process Biochemistry, vol. 50, p. 194-204.
Suwannakham, Construction and characterization of ack knock-out mutants of Propionibacterium acidipropionici for enhanced propionic acid fermentation, Feb. 2006, Biotechnology and Bioengineering, vol. 94, p. 383-395.
Suwannakham, Enhanced propionic acid fermentation by Propionibacterium acidipropionici mutant obtained by adaptation in a fibrous-bed bioreactor, Jun. 2005, Biotechnology and Bioengineering, Vo. 91, p. 325-337.
Suwannakham, Metabolic engineering for enhanced propionic acid fermentation by Propionibacterium acidipropionici, 2005, Ohio State University, 34 pages.
Tufvesson et al., Economic and environmental assessment of propionic acid production by fermentation using different renewable raw materials, Dec. 2013, Bioresource Technology, vol. 149, p. 556-564.
Thierry et al., New insights into physiology and metabolism of Propionibacterium freudenreichii, Jan. 2011, International Journal of Food Microbiology, vol. 149, p. 19-27.

(Continued)

*Primary Examiner* — Christian L Fronda
(74) *Attorney, Agent, or Firm* — Fish & Richardson P.C.

(57) ABSTRACT

Microbial cell lines suitable for industrial-scale production of organic acids and methods of making and isolating such cell lines.

16 Claims, 2 Drawing Sheets

Specification includes a Sequence Listing.

(56) References Cited

OTHER PUBLICATIONS

Scholz, et al., The natural history of cutaneous propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov., 2016, International Journal of Systematic and Evolutionary Microbiology, vol. 66, p. 4422-4432.

Rehberger et al., Response of cultures of Propionibacterium to Acid and Low pH: Tolerance and Inhibition, 1998, Journal of Food Production, vol. 61, p. 211-216.

Ahmadi et al., An overview of biotechnological production of propionic acid: From upstream to downstream processes, 2017, Electronic Journal of Biotechnology, vol. 28, p. 67-75.

Guan, Understanding of how Propionibacterium acidipropionici respond to propionic acid stress at the level of proteomics, 2014, Scientific Reports, vol. 4, 6951, 8 pages.

Guan, Metabolic engineering of acid resistance elements to improve acid resistance and propionic acid production of Propionibacterium jensenii, 2016, Biotechnology and Bioengineering, vol. 113, p. 1294-304.

Jiang et al., Enhanced propionic acid production from whey lactose with immobilized Propionibacterium acidipropionici and the role of trehalose synthesis in acid tolerance, 2015, Green Chemistry, vol. 15, p. 250-259.

International Search Report and Written Opinion in International Application No. PCT/US2019/37520, dated Oct. 29, 2019, 17 pages.

\* cited by examiner

SEQUENCE LISTING

<160> NUMBER OF SEQ ID NOS: 29

<210> SEQ ID NO 1
<211> LENGTH: 258
<212> TYPE: PRT
<213> ORGANISM: Propionibacterium acidi-propionici -continued

<400> SEQUENCE: 1

Met Ser Asp Gly Gly Ile Ser Pro Gly Asp Arg Leu Ala Arg Ala His
1               5                   10                  15

Ser Phe Gly Glu Ala Ala Asp Tyr Gln Arg Tyr Arg Pro Asp Tyr
            20                  25                  30

Pro Ile Glu Ala Val Thr Tyr Leu Val Ala Gly Thr Pro Ala Gly Gly
            35                  40                  45

Arg Val Leu Asp Leu Gly Ala Gly Thr Gly Lys Leu Thr Asp Arg Leu
50                  55                  60

Val Ala Leu Gly Phe Glu Val Ala Val Asp Pro Ser Ala Gln Met
65              70                  75                  80

Leu Ala Glu Leu Ser Arg Arg Pro Asp Val Asp Cys Arg Val Gly
                85                  90                  95

Thr Gly Glu Ser Leu Pro Leu Pro Asp Ser Cys Val Asp Gly Val Val
                100                 105                 110

Cys Gly Gln Ala Trp His Trp Met Asp Ala Gly Ala Val Gly Arg Glu
                115                 120                 125

Leu Ala Arg Val Met Arg Pro Asn Gly Ser Leu Gly Leu Ala Trp Asn
130                 135                 140

Thr Asp His Thr Asp Thr Gly Trp Leu Ala Arg Ile Glu Ala Ile Arg
145                 150                 155                 160

Asn Val Pro Arg Gly Ala Glu Leu Asn Arg Gly Pro Asp Arg Thr Pro
                165                 170                 175

Val Ser Pro Gly Gln Gly Trp Ser Pro Phe Thr Arg His Asp Val Asp
                180                 185                 190

Trp Thr Arg Thr Met Thr Lys Glu Asp Phe Leu Ala Leu Trp Arg Thr
            195                 200                 205

His Ser Gln Trp Leu Thr Ala Thr Glu Glu Arg Ile Arg Trp Met
    210                 215                 220

Ser Gly Trp Arg Asp Val Leu Ala Thr Asp Pro Gln Val Ala Thr Leu
225                 230                 235                 240

Asp Thr Val Ser Ile Pro Met Thr Thr Glu Cys Trp Val Thr Arg Pro
                245                 250                 255

Gly Gly

<210> SEQ ID NO 2
<211> LENGTH: 412
<212> TYPE: PRT
<213> ORGANISM: Propionibacterium acidi-propionici

<400> SEQUENCE: 2

Met Leu Gly Asp Ala Thr Gly Arg Leu Arg Val Gly Glu Gln Lys Gln
1               5                   10                  15

Ala Gly Arg Gly Leu Ser Arg Gly Leu Leu Leu Met Ala Thr Ala
            20                  25                  30

Thr Gly Leu Ala Val Gly Gly Asn Tyr Leu Asn Gln Pro Leu Ile Asp
            35                  40                  45

Glu Ile Ala Arg His Phe Ser Val Ser Val Ser Thr Ala Ala Thr Ser
    50                  55                  60

Val Thr Val Thr Gln Phe Ala Tyr Ala Leu Gly Leu Val Leu Phe Val
65                  70                  75                  80

Pro Leu Gly Asp Met Ile Asn Arg Arg Lys Leu Ala Val Thr Leu Phe
                85                  90                  95

-continued

```
Leu Val Ser Ala Ala Gly Leu Leu Thr Ala Ala Val Ser Gly Ser Phe
                100                 105                 110

Ala Val Met Met Ile Gly Thr Ala Ile Ala Ser Leu Phe Ser Val Ala
            115                 120                 125

Ala Gln Val Leu Val Pro Phe Ala Ser Glu Leu Ala Ala Pro Gly Arg
        130                 135                 140

Gly Gly Ala Ala Val Gly Thr Met Met Thr Gly Leu Leu Thr Gly Ile
145                 150                 155                 160

Leu Val Ala Arg Ala Val Ser Gly Met Leu Ser Leu Val Gly Gly Trp
                165                 170                 175

Lys Thr Ala Tyr Trp Val Leu Gly Val Leu Leu Leu Val Met Ala Ala
            180                 185                 190

Thr Leu Trp Lys Met Leu Pro Asp Val Pro Val Ala Glu Ser Phe Ser
        195                 200                 205

Leu Thr Arg Val Pro Ala Ser Met Gly Arg Ala Trp Met Arg Tyr Pro
210                 215                 220

Lys Val Arg Ser Arg Ala Val Ile Ser Ala Leu Leu Phe Ala Ser Val
225                 230                 235                 240

Ser Ala Cys Phe Ala Thr Met Thr Pro Leu Leu Ala Gly Pro Pro His
                245                 250                 255

Arg Leu Gly Pro Gly Val Ile Gly Ile Leu Gly Leu Leu Gly Leu Val
            260                 265                 270

Gly Ala Phe Ala Ala Gly Pro Val Gly Arg Met Ala Asp Arg Gly Leu
        275                 280                 285

Gly Asn Arg Thr Val Val Leu Gly Leu Val Ile Leu Ala Ala Gly Trp
    290                 295                 300

Ala Ser Met Trp Phe Ala Thr Gly Ser Val Val Met Phe Gly Ile Gly
305                 310                 315                 320

Phe Ile Leu Thr Asp Leu Gly Leu Gln Ser Ala His Val Thr Asn Met
                325                 330                 335

Asn Val Val Tyr Ala Gln Glu Pro Ala Leu Arg Ser Arg Leu Asn Ser
            340                 345                 350

Leu Tyr Met Thr Met Tyr Phe Ile Gly Gly Ser Val Gly Ser Ala Val
        355                 360                 365

Ala Val Gly Leu Trp Ser Arg Phe Ala Trp His Gly Val Val Ile Ala
    370                 375                 380

Ala Leu Ala Phe Val Thr Ala Ala Gly Val Val Phe Ala Leu Glu Arg
385                 390                 395                 400

Leu Ser Asp Arg Arg Pro Arg Ile Ala Ser Gln Gly
                405                 410

<210> SEQ ID NO 3
<211> LENGTH: 264
<212> TYPE: PRT
<213> ORGANISM: Propionibacterium acidi-propionici

<400> SEQUENCE: 3

Met Ala Leu Leu Ile Ile Leu Ile Leu Val Val Val Ile Gly Gly
1               5                   10                  15

Gly Val Gly Leu Phe Ile Ala Pro Tyr Asn Ser Phe Val Lys Leu Arg
            20                  25                  30

Asn Thr Ile Gln Glu Ser Trp Arg Gln Val Asp Val Glu Leu Asn Arg
        35                  40                  45

Arg Tyr Glu Leu Ile Pro Asn Leu Val Glu Thr Val Arg Ala Gly Ala
    50                  55                  60
```

Ala His Glu Arg Asn Thr Leu Glu Glu Val Thr Arg Leu Arg Asn Gln
65                  70                  75                  80

Ala Val Ala Met Ala Thr Asn Ser Gln Gly Asn Thr Pro Asp Pro Gln
                85                  90                  95

Arg Ser Gln Ile Glu Ser Gln Leu Ser Gly Ala Val His Asn Leu Val
            100                 105                 110

Ala Gln Val Glu Ala Tyr Pro Glu Leu Arg Ser Asn Thr Asn Phe Leu
        115                 120                 125

Glu Leu Gln Arg Glu Leu Ser Asp Thr Glu Asp Arg Ile Ala Ala Gly
    130                 135                 140

Arg Arg Tyr Tyr Asn Ala Asn Val Lys Thr Tyr Asn Thr Lys Val Glu
145                 150                 155                 160

Ser Phe Pro Ser Asn Leu Val Ala Gly Met Phe His Phe Glu Lys Ala
                165                 170                 175

Ser Tyr Phe Gln Val Asp Asp Pro Ala Val Arg Ser Ala Pro Gly Val
            180                 185                 190

Asn Phe Gly Glu Ile Ser Gln Arg Pro Glu Ala Gln Asn Gln Gly
        195                 200                 205

Gln Ala Pro Gln Ile Gly Gln Gly Asn Pro Ala Gln Ala Pro Gly Tyr
    210                 215                 220

Ala Ala Pro Gln Ala Ser Gly Gln Leu Pro Asp Pro Gln Ala Ala Arg
225                 230                 235                 240

Gln Pro Asp Pro Ser Gln Gln Pro Trp Gly Thr Gln Gly Lys Pro Gly
                245                 250                 255

Asp Gln Gly Asn Gln Asn Ser Gln
            260

<210> SEQ ID NO 4
<211> LENGTH: 166
<212> TYPE: PRT
<213> ORGANISM: Propionibacterium acidi-propionici

<400> SEQUENCE: 4

Met Ser Ala Asn Pro Val Pro Gln Val Pro Gly Thr Gly Thr Leu Leu
1               5                   10                  15

Ala Asp Val Phe Arg Trp His Pro Ala Gly Val Ala Val Leu Thr Ala
                20                  25                  30

Asp Gly Pro Ser Arg Pro Val Gly Ile Thr Val Ser Ser Leu Ala Ser
            35                  40                  45

Val Ser Val Ala Pro Pro Met Val Ser Val Ser Met Ala Asn Ser Ser
        50                  55                  60

Thr Thr Leu Ala Ala Leu His Leu Gly Gly Arg Ala Val Val His Leu
65                  70                  75                  80

Leu Asp Ala Gly Gln Glu Asp Leu Ala Asp Ser Phe Ala Arg Pro Gly
                85                  90                  95

Val Pro Ala Val Gly Ile Asp Trp Glu Arg Thr Ala Glu Asn Ala Pro
            100                 105                 110

Gln Leu Asp Val Glu Thr Pro Arg Leu His Ala Val Ala Arg Met
        115                 120                 125

Ile Asp Thr Gly Ser Ala Thr Leu Val Ala Leu Thr Ile Glu Arg Ile
    130                 135                 140

Glu Val Gly Arg Arg Gly Ser Ala Ala Leu Val Arg Met Gly Arg Gly
145                 150                 155                 160

Trp Tyr Thr Leu Pro Arg
            165

```
<210> SEQ ID NO 5
<211> LENGTH: 210
<212> TYPE: PRT
<213> ORGANISM: Propionibacterium acidi-propionici

<400> SEQUENCE: 5

Met Ser Glu Gln Thr Ser Pro Ala Ser Pro Thr Pro Gly Pro Arg Pro
1               5                   10                  15

Val Thr Glu Ile Gly Thr Leu Pro Pro Ile Asp Val Val Glu Lys Arg
            20                  25                  30

Leu Pro Val Asp Pro Ala Thr Gly Arg Pro Arg Arg Glu Ile Leu Ala
        35                  40                  45

Thr Ile Ala Thr Ile Cys Tyr Ile Leu Ala Ala Gly Ala Ser Ala Val
    50                  55                  60

Ala Leu Ala Arg Ala Trp Trp Gly Thr Ile Asn Met Arg Thr Phe His
65                  70                  75                  80

Leu Ala Thr Asn Leu Met Thr Trp Thr Asp Pro Arg Pro Gly Ser Leu
                85                  90                  95

Ala Ser Val Leu Leu Ala Ala Leu Met Met Val Ile Gly Gly Val Met
            100                 105                 110

Val Ala Met Pro Ala Leu Leu Ala Val Asn Thr Trp Leu Gly Arg Arg
        115                 120                 125

Trp Val Arg Trp Gly Ala Ile Gly Gly Val Ala Ala Val Leu Ala
    130                 135                 140

Val Thr Leu Asn Pro Leu Ala Trp Ile Ser Ala Pro Phe Ser Ile Ala
145                 150                 155                 160

Gly Gly Val Met Val Trp Leu Pro Ser Thr Arg Arg Trp Phe Glu Leu
                165                 170                 175

Trp Arg Gln Val Arg Ser Glu Pro Glu Val Glu Arg Phe Thr Pro Arg
            180                 185                 190

Pro Ile Thr Tyr Gly Pro Val Ala Lys His Met Trp Pro Pro Gly Arg
        195                 200                 205

Arg Thr
    210

<210> SEQ ID NO 6
<211> LENGTH: 390
<212> TYPE: PRT
<213> ORGANISM: Propionibacterium acidi-propionici

<400> SEQUENCE: 6

Met Ser Gln Gly Glu Pro Gly Tyr Arg Arg Ala Ser Leu Ala Leu Leu
1               5                   10                  15

Ala Ala Gly Leu Ala Ser Phe Asn Ala Leu Tyr Cys Thr Gln Ala Leu
            20                  25                  30

Met Pro Thr Leu Thr Ser Gln Leu Gly Ala Thr Pro Ala Gln Ala Ser
        35                  40                  45

Leu Thr Val Ser Ala Ala Thr Gly Ile Leu Ala Ile Thr Ile Leu Pro
    50                  55                  60

Val Ser Val Leu Ser Glu Arg Phe Gly Arg Gly Arg Leu Met Thr Ile
65                  70                  75                  80

Ser Ala Met Ala Ala Val Val Val Gly Leu Leu Leu Pro Leu Ala Pro
                85                  90                  95

Ser Leu Gly Trp Leu Val Val Gly Arg Gly Leu Gln Gly Leu Leu Val
            100                 105                 110
```

Ala Gly Val Pro Ala Thr Ala Met Ala Trp Leu Ser Gln Glu Ile His
            115                 120                 125

Pro Arg His Leu Pro Arg Ala Met Gly Leu Tyr Val Ala Gly Asn Thr
        130                 135                 140

Val Gly Leu Leu Gly Arg Leu Ile Pro Ser Gly Val Leu Gln Phe
145                 150                 155                 160

Thr Gly Trp Arg Pro Ala Leu Gly Ile Asp Met Ala Phe Ala Leu Val
                165                 170                 175

Cys Thr Val Ala Met Val Thr Leu Met Pro Ala Glu Arg Arg Phe Val
            180                 185                 190

Pro Lys Gln Leu Arg Pro Gly Asn Glu Leu Arg Thr Met Gly Arg Gln
        195                 200                 205

Trp Ala Asp Arg Arg Leu Ala Gly Leu Phe Gly Ile Gly Phe Ile Phe
210                 215                 220

Met Gly Val Phe Val Ser Leu Tyr Asp Phe Leu Gly Tyr Arg Leu Thr
225                 230                 235                 240

Ala Arg Phe Gly Met Pro Pro Ser Leu Ile Gly Leu Val Phe Leu Leu
                245                 250                 255

Tyr Leu Phe Gly Thr Leu Ala Ser Ala Arg Ala Gly His Leu Thr Ala
            260                 265                 270

Thr Arg Gly Arg Gly Pro Ala Met Leu Ile Gly Ala Ala Met Ala Ile
        275                 280                 285

Val Gly Met Pro Leu Val Ala Ser Gly Leu Leu Trp Leu Thr Leu Pro
290                 295                 300

Gly Val Ala Leu Phe Thr Tyr Gly Phe Phe Thr Val His Ser Val Ala
305                 310                 315                 320

Ser Gly Trp Val Gly Ala Leu Ala Pro Arg Ala Arg Gly Glu Ala Ser
                325                 330                 335

Gly Thr Tyr Leu Ala Cys Tyr Tyr Leu Gly Ser Ser Ile Leu Gly Tyr
            340                 345                 350

Leu Ser Gly His Val Met His Ala Phe Gly Trp Thr Gly Leu Val Met
        355                 360                 365

Trp Leu Val Gly Leu Ile Leu Ile Gly Cys Ala Leu Ser Ala Met Val
370                 375                 380

Val Arg Ser Ala Arg Ser
385                 390

<210> SEQ ID NO 7
<211> LENGTH: 391
<212> TYPE: PRT
<213> ORGANISM: Propionibacterium acidi-propionici

<400> SEQUENCE: 7

Met Ala Ala Thr Ala Thr Arg Pro Pro Arg Asp Arg Arg Pro Ser Val
1               5                   10                  15

Val His Leu Ser Thr Val His Asn Arg His Asp Asn Arg Val Phe Asn
            20                  25                  30

Lys Glu Ala Arg Ala Leu Val Asn Ala Gly Tyr Asp Phe His Leu Val
        35                  40                  45

Ile Ser Ala Asp Ala Asp Gly Val Asp Asp Gly Ile Pro Val Val Gly
    50                  55                  60

Leu His Arg Thr Val Gly Pro Arg Leu Arg Ile Val Ala Gly Gln
65                  70                  75                  80

Leu Glu Ala Trp Arg Val Leu Gly Ser Leu Arg Pro Glu Leu Leu Gln
                85                  90                  95

-continued

```
Ile His Asp Pro Glu Leu Ile Pro Met Ala Leu Leu Trp Gly Arg Thr
            100                 105                 110
His Pro Cys Lys Val Val Tyr Asp Ala His Glu Asp Leu Val Gly Gln
        115                 120                 125
Ile Asp Thr Lys Pro Tyr Leu Asn Arg Leu Thr Arg Pro Val Ala Arg
    130                 135                 140
Ala Ala Ala Arg Cys Leu Val Gly Met Ala Asp Arg Gly Ala Asp Gly
145                 150                 155                 160
Ile Val Ala Ala Thr Glu Pro Val Ala Asp Arg Phe Arg Asn Pro Arg
                165                 170                 175
Ile Ala Val Val His Asn Tyr Pro Trp Leu Ala Asn Phe Thr Val Asp
            180                 185                 190
Pro Ala Pro Val Pro Gly Arg Leu Val Tyr Ala Gly Asp Leu Ser Gln
        195                 200                 205
Glu Arg Lys Leu Ser Phe Met Ile Asp Val Val Arg Ala Leu Arg Ala
    210                 215                 220
Thr Val Pro Ala Ala His Leu Val Leu Ala Gly Arg Ala Leu Lys Gly
225                 230                 235                 240
Cys Gly Pro Val Val Glu Ala Gly Val Ala Glu Gly Leu Val Asp Tyr
                245                 250                 255
Arg Gly Leu Val Gly Pro Thr Glu Val Pro Gly Val Leu Ala Ser Ala
            260                 265                 270
Gln Val Gly Leu Val Phe Leu Glu Pro Leu Pro Asn Tyr Val Arg Ser
        275                 280                 285
Leu Pro Thr Lys Leu Phe Glu Tyr Met Ala Ala Gly Val Pro Phe Cys
    290                 295                 300
Ala Ser Asp Phe Pro Ala Trp Ser Gln Met Phe Ser Gly Tyr Gly Ala
305                 310                 315                 320
Gly Ala Phe Ala Asp Ser Glu Ser Val Glu Thr Thr Ala Asn Val Leu
                325                 330                 335
Ala Gly Leu Leu Thr Asp Pro Gln Gly Cys Glu Gln Met Gly Glu Ala
            340                 345                 350
Gly Arg Arg Ala Ile Gly Glu Gly Leu Thr Phe Glu Ala Gln Ser Arg
        355                 360                 365
Ala Leu Leu Thr Leu Thr Glu Glu Leu Leu Gly Cys Gly Ala Gly Pro
    370                 375                 380
Leu Gly Gly Gly Glu Arg Gln
385                 390

<210> SEQ ID NO 8
<211> LENGTH: 451
<212> TYPE: PRT
<213> ORGANISM: Propionibacterium acidi-propionici

<400> SEQUENCE: 8

Met Gly Ala Cys Ala Glu Ala Leu Leu Trp Leu Leu Phe Ile Val Leu
1               5                   10                  15
Thr Phe Ile Ser Thr Asp Gln Ala Ile Ala Ser Asp Arg Ala Tyr Pro
            20                  25                  30
Met Leu Leu Val Val Leu Gly Val Ala Gly Ala Gly Cys Leu Val Leu
        35                  40                  45
Gly Val Leu Arg Arg Arg Glu Gly Arg Ser Ala Val Ser Gly Ser Gly
    50                  55                  60
Ile Gly Arg Pro Gly Trp Arg Ala Leu Gly Leu Thr Ala Leu Pro Phe
65                  70                  75                  80
```

```
Leu Ala Met Leu Cys Trp Ala Gly Ile Thr Ile Pro Phe Ala Thr His
                 85                  90                  95
Val Ala Leu Ser Asn Arg Phe Gly Pro Leu Val His Ile Arg Leu Pro
            100                 105                 110
Met Ala Ser Met Val Val Pro Leu Val Glu Ala Ala Leu Val Val Leu
            115                 120                 125
Val Ala Val Gly Leu Val Val Gly Ile Gly Arg Arg Leu Pro Glu
            130                 135                 140
Ala Leu Trp Arg Ala Phe Leu Val Leu Ala Ala Ser Thr Leu Ile Ser
145                 150                 155                 160
Ile Val Trp Gln Val Ala Thr Arg His Ala Met Val Arg Arg Ala Val
                165                 170                 175
Asp Gly Lys Leu Met Trp Arg Thr Ser Thr Gln Leu Gly Gly Gln Ala
            180                 185                 190
Thr Tyr His Leu Ala Leu Leu Gly Ile Gly Val Ala Val Asp Ala
            195                 200                 205
Ile Arg Arg Arg Tyr Arg Val Gly Val Ser Trp Leu Ile Ile Ala Gly
            210                 215                 220
Leu Gly Leu Ala Ile Val Leu Ser Gly Ser Arg Ala Gly Leu Ile Cys
225                 230                 235                 240
Leu Gly Leu Phe Cys Val Ala Leu Phe Ile Trp Gly Arg Pro Ala Gly
                245                 250                 255
Gly Arg Gly Gly Gly Arg Arg Arg Thr Leu Val Gly Val Leu Gly
            260                 265                 270
Leu Ala Ala Leu Ala Val Ala Gly Ala Leu Leu Trp Leu Arg Gly
275                 280                 285
Gly Ala Leu Val Asp His Asp Arg Ala Gln Thr Trp Lys Val Ala Trp
            290                 295                 300
Arg Ala Val Thr Ala Asp Pro Thr Thr Val Ile Val Gly Arg Gly Tyr
305                 310                 315                 320
Ala Thr Ile Trp Pro Trp Phe Ala Thr Glu Thr Gly Ile Val Pro Gly
                325                 330                 335
Ala Ile His Gly Leu Arg Pro Gly Pro Phe Gly Lys Ser Leu Val His
            340                 345                 350
Ala His Asn Thr Val Val Gln Val Gly Gly Glu Leu Gly Ile Ile Gly
            355                 360                 365
Leu Val Leu Leu Leu Val Ser Val Gly Val Ala Val Leu Ala Phe
            370                 375                 380
Arg Gly Ile His Gly Arg His Leu Gly Ile Cys Leu Ala Leu Leu Ala
385                 390                 395                 400
Ser Leu Pro Ala Leu Val Leu Asp Thr Tyr Leu Val Lys Asn Phe Gln
                405                 410                 415
Val Ser Leu Val Trp Trp Leu Ala Ala Ala Val Ala Val Leu Met
            420                 425                 430
Ala Arg Pro Ala Asp His Asp Gln Pro Thr Asn Ser Asp Gln Pro Ala
            435                 440                 445
Asp Arg Pro
    450

<210> SEQ ID NO 9
<211> LENGTH: 455
<212> TYPE: PRT
<213> ORGANISM: Propionibacterium acidi-propionici
```

-continued

<400> SEQUENCE: 9

Met Ser Arg Arg Ala Phe Arg Tyr Arg Asp Thr Thr Pro Gly Thr Val
1               5                   10                  15

Leu Gly Val Val Ala Ala Met Leu Val Leu Arg Leu Pro Leu Ser Phe
            20                  25                  30

Leu Leu Phe Val Val Ala Pro Trp Phe Leu Ile Leu Thr Gly Ala Ile
        35                  40                  45

Ala Lys Gly Gly Ser Val Arg Cys Leu Pro Leu Lys Ala Met Leu Gly
    50                  55                  60

Trp Cys Leu Val Ala Ala Thr Ile Ser Ile Ala Val Leu His Pro Gly
65                  70                  75                  80

Val Ala Ala Ser Thr Gly Asn Asn Val Val Ile Met Ile Ala Val Ile
                85                  90                  95

Gly Cys Thr Leu Val Val His Arg Gly Gln Ala Pro Gly Leu Thr Ala
            100                 105                 110

Arg Arg Thr Leu Ala Gly Leu Tyr Trp Gly Ala Gly Gly Val Trp Leu
        115                 120                 125

Ile Ala Met Gly Glu Met Ile Thr Gly Ile Lys Leu Leu Pro Ile Leu
    130                 135                 140

Tyr Pro Asp Ala Asn Thr Val Ser Tyr Val Gln Ser Ser Arg Phe Ile
145                 150                 155                 160

Val Ser Ala Thr Tyr Pro Asn Ile Asn Asp Phe Ser Val Leu Val Val
                165                 170                 175

Met Leu Val Thr Ala Val Val Ala Arg Met Trp Phe Asp Arg Ala Arg
            180                 185                 190

Gly Trp Arg Asn Ala Gly Arg Trp Leu Val Leu Leu Thr Ser Leu Phe
        195                 200                 205

Met Val Val Met Ser Thr Ser Arg Gly Ala Leu Val Gly Cys Leu Ala
    210                 215                 220

Gly Val Ala Leu Leu Ile Val Leu Asn Val Arg Arg Leu His Pro His
225                 230                 235                 240

Ala Leu Gly Val Arg Ala Gly Leu Phe Gly Gly Gly Leu Ile Val Phe
                245                 250                 255

Val Gly Ala Val Phe Phe Thr Ser Ser Tyr Val Gln Asp His Ser Thr
            260                 265                 270

Ala Thr Arg Gly Gln Ile Phe Asn Asn Ala Met Ser Met Leu Ala Gly
        275                 280                 285

Ser Pro Ala Asp Ala Leu Leu Gly Tyr Gly Ser Leu Ala Ser Tyr Gln
    290                 295                 300

Ser Ala Ala Lys Ala Ala Phe Gly Asp Val Leu Met Asp Pro His Asn
305                 310                 315                 320

Met Leu Leu Glu Ile Thr Leu Asn Tyr Gly Val Ile Ala Leu Val Leu
                325                 330                 335

Phe Ile Val Val Trp Leu Trp Val Leu Met Arg Gly Phe Leu Pro Arg
            340                 345                 350

Arg Pro Met Ala Asp Trp Gln Thr Ala Phe Gly Leu Thr Thr Val Val
        355                 360                 365

Leu Leu Pro Leu Leu Gly Val Val Pro Ser Ser Thr Leu Arg Tyr His
    370                 375                 380

Val Thr Trp Ile Tyr Leu Ala Ala Thr Thr Leu Leu Val Ala Glu Gly
385                 390                 395                 400

```
Ala Glu Ala Arg Thr Pro Thr Arg Pro Glu Leu Ser Asp Glu Gln Pro
            405                 410                 415

Ser Gly Arg Glu Leu Ser Gly Ser Asp Thr Ser Gly Ala Thr Ala Ala
        420                 425                 430

Asp Gly Asp Leu Gly His Ala His Asp His Ala Arg Asp Gln Ala
        435                 440                 445

Glu His His Ser Asp His Arg
    450                 455

<210> SEQ ID NO 10
<211> LENGTH: 437
<212> TYPE: PRT
<213> ORGANISM: Propionibacterium acidi-propionici

<400> SEQUENCE: 10

Met Ala Arg Arg His Gly Leu Ile Gly Gly Trp Arg Glu Pro Met Gly
1               5                   10                  15

Arg Gln Arg Val Trp Leu Pro Val Ala Gly Leu Ser Ala Leu Leu Val
            20                  25                  30

Val Glu Thr Phe Phe Asp Leu Arg Arg Ser Met Thr Pro Ser Pro Trp
        35                  40                  45

Leu Trp Asn Ser Tyr Leu Ile Val His Leu Leu Ala Ala Leu Ala Cys
    50                  55                  60

Leu Val Leu Ile Leu Ala Gly Arg Asp Gly Asn Arg Phe Ser Arg Ala
65                  70                  75                  80

Gly Trp Ile Val Ile Gly Phe Ala Ala Ala Leu Met Ala Cys Ser Leu
                85                  90                  95

Val Ser Ala Ala Val Thr Pro Leu Pro Arg Val Ser Tyr Val Thr Val
            100                 105                 110

Pro Arg Ala Tyr Leu Val Val Pro Thr Leu Thr Ala Ala Ala Thr Leu
        115                 120                 125

Leu Leu Gly Ala Ala Val Val Arg Val Leu Pro Asp Gln Pro Val His
    130                 135                 140

Arg Val Leu Trp Trp Pro Ala Ala Leu Thr Leu Ala Cys Ala Phe Ala
145                 150                 155                 160

Gln Trp Pro Arg Ser Ala Val Val His Gly Ser Pro Arg Leu Ala Thr
                165                 170                 175

Gly Met Gly Gly Ser Ala Val Val His Val Pro Leu Leu Leu Ala Thr
            180                 185                 190

Gly Val Ala Leu Ala Ala Phe Leu Ala Gly Trp Arg Arg Trp Trp Ser
        195                 200                 205

Leu Gly Leu Thr Val Ile Gly Val Ala Ala Val Val Leu Thr Gly Ser
    210                 215                 220

Arg Ser Gly Val Val Cys Leu Val Leu Ala Gly Val Val Gly Leu
225                 230                 235                 240

Gln Trp Leu Arg Ser Arg Arg Ala Trp Leu Val Ala Gly Ala Ala Val
                245                 250                 255

Val Ala Leu Gly Ile Val Val Ala Ala Val Pro Met Leu His Arg Leu
            260                 265                 270

Leu Asn Pro Thr Asp Glu Leu Arg Ala Lys Asn Leu Glu Thr Ala Leu
        275                 280                 285

Gly Val Trp Thr Glu Thr Pro Lys His Leu Leu Leu Gly Val Gly Ser
    290                 295                 300

Gly Arg Leu Trp Pro Trp Tyr Ala Phe Asp Ser His Leu Leu Arg Thr
305                 310                 315                 320
```

```
Pro Trp Arg Gly Met Val Thr Thr Glu Trp Gly Pro Ala Leu Asn Ser
            325                 330                 335

Ala His Ser Thr Phe Leu Gln Val Leu Val Glu Leu Gly Leu Leu Gly
            340                 345                 350

Met Leu Leu Leu Ile Pro Val Val Val Pro Val Val Leu Ala
            355                 360                 365

Arg Arg Leu Trp Pro Gly Leu Arg Gly Ala Ala Arg Pro Val Pro Asp
            370                 375                 380

Thr Val Pro Leu Ile Ala Leu Val Ala Thr Pro Ala Phe Phe Leu
385                 390                 395                 400

Asp Thr Tyr Leu Leu Lys Asn Tyr Gly Ala Ser Leu Trp Trp Trp Leu
            405                 410                 415

Val Val Leu Arg Cys Leu Arg Arg Ala Gln Ser Ala Pro Ser Thr Ser
            420                 425                 430

Val Gln Asn Arg Gly
            435

<210> SEQ ID NO 11
<211> LENGTH: 767
<212> TYPE: PRT
<213> ORGANISM: Propionibacterium acidi-propionici

<400> SEQUENCE: 11

Met Ala Glu Pro Arg His Ala Gly Arg Gly Ala Arg His Gly Lys
1               5                   10                  15

Ala Lys Arg Arg Lys Gly Ser Pro Phe Gly Arg Phe Val Lys Arg Thr
            20                  25                  30

Leu Phe Ser Leu Leu Ile Leu Val Val Leu Ala Ile Ala Ala Gly
            35                  40                  45

Val Gly Ala Ile Val Phe Tyr Asn Arg Thr Asn Leu Pro Asp Pro Asn
    50                  55                  60

Lys Asp Phe Gln Thr Asn Thr Ser Phe Ile Tyr Phe Asn Asp Ser Lys
65              70                  75                  80

Thr Lys Leu Gly Ser Leu Ser Val Gln Asn Arg Gln Thr Ile Ser Tyr
            85                  90                  95

Glu Gln Met Pro Lys Ser Ile Lys Asp Ala Ala Ile Ser Ala Glu Asn
            100                 105                 110

Arg Thr Phe Trp Glu Asp Gln Gly Ile Ser Ile Gly Gly Ile Val Arg
            115                 120                 125

Ala Ala Trp Thr Ile Ala Arg Gly Gly Glu Met Gln Gly Gly Ser Thr
        130                 135                 140

Ile Thr Gln Gln Tyr Ile Lys Ile Leu Tyr Leu Ser Gln Asp Arg Thr
145             150                 155                 160

Met Gln Arg Lys Leu Lys Glu Leu Val Leu Ala Val Lys Met Gly Lys
            165                 170                 175

Gln Val Pro Lys Glu Asp Ile Leu Ala Gly Tyr Leu Asn Thr Ile Tyr
            180                 185                 190

Phe Gly Arg Gly Ala Tyr Gly Ile Gln Ala Ala Lys Ser Tyr Phe
            195                 200                 205

Asn Val Asp Ala Ser Lys Leu Thr Val Pro Gln Ser Ala Val Leu Ala
        210                 215                 220

Ser Ile Leu Asn Asn Pro Thr Leu Phe Asp Ala Ser Gly Gly Thr Lys
225             230                 235                 240

Ala Arg Glu Arg Leu Leu Asn Arg Tyr Arg Tyr Val Leu Asp Gly Met
            245                 250                 255
```

-continued

Leu Glu Ala Gly Asn Ile Thr Gln Ala Gln His Asp Glu Tyr Ser Arg
                260                 265                 270
Lys Leu Pro Ala Phe Pro Glu Val Pro Ile Asn Asn Arg Trp Gly Gly
            275                 280                 285
Thr Asn Gly Tyr Leu Leu Lys Met Val Gln Asn Glu Leu Leu Asp Asp
        290                 295                 300
Gly Phe Thr Asp Ser Gln Ile Asn Gly Gly Leu Lys Val Thr Thr
305                 310                 315                 320
Thr Phe Asp Pro Ala Ala Gln Lys Ala Ala Val Ala Thr Gly Gln Lys
                325                 330                 335
Tyr Lys Lys Leu Ala Gly Ser Asn Ala Gly Lys Asn Gly Ala Lys Asn
            340                 345                 350
Leu His Pro Ala Ile Ala Ser Val Lys Val Gly Thr Gly Glu Val Leu
        355                 360                 365
Ala Leu Tyr Gly Gly Asp Asp Tyr Ile Thr Ser Thr Arg Ser Trp Ala
    370                 375                 380
Leu Gln Ala Arg Pro Ala Ala Ser Thr Phe Lys Thr Tyr Ala Val Ile
385                 390                 395                 400
Ala Gly Met Arg Asn Gly Phe Ser Leu Lys Ser Lys Leu Asn Gly Asp
                405                 410                 415
Thr Phe Thr Pro Gln Gly Asp Ser Val Pro Ile Arg Asn Glu Phe Ser
            420                 425                 430
Glu Gln Tyr Gly Asp Val Thr Leu Gln Lys Ala Thr Glu Asp Ser Ile
        435                 440                 445
Asn Thr Ala Phe Val Asp Met Met Thr Gln Ile Asp Asn Gly Pro Gln
    450                 455                 460
Ala Met Leu Lys Ala Ala Asn Asp Ala Gly Val Pro Lys Gly Ser Gly
465                 470                 475                 480
Trp Asp Leu Asn Asn Arg Met Pro Leu Gly Val Ala Glu Val Ser Pro
                485                 490                 495
Leu Asp Gln Ala Thr Gly Tyr Ala Thr Ile Ala Asn Glu Gly Lys Tyr
            500                 505                 510
Val Pro Ser His Val Val Ala Lys Val Thr Asp Ser Ser Gly Lys Thr
        515                 520                 525
Leu Tyr Thr Ala Lys Thr Thr Gly Lys Gln Thr Ile Gln Lys Asp Ile
    530                 535                 540
Ala His Asp Thr Thr Tyr Ala Leu Glu Asn Val Val Asn Glu Gly Thr
545                 550                 555                 560
Gly Ser Ala Val Ser Asn Leu Gly Tyr Pro Val Ala Gly Lys Thr Gly
                565                 570                 575
Thr Asn Gly Val Lys Asp Asp Ile Thr Ser Ala Trp Phe Val Ala Tyr
            580                 585                 590
Thr Arg Gln Ile Ser Thr Ala Val Met Tyr Val Ala Gly Asp Ser Gly
        595                 600                 605
Asn Ala Asp Leu Asp Pro Tyr Ala Ala Pro Gly Asp Ala Thr Phe Phe
    610                 615                 620
Gly Gly Thr Tyr Pro Ala Arg Thr Trp Ala Asp Tyr Met Lys Val Ala
625                 630                 635                 640
Met Lys Gly Leu Pro Ala Lys Asp Phe Pro Asp Pro Asp Trp Val Asn
                645                 650                 655
Leu Ser Gly Asn His Tyr Gly Asp Thr Gln Arg Glu Thr Leu Arg Thr
            660                 665                 670

```
Pro Thr Pro Thr Pro Thr Pro Thr Gln Ala Pro Thr Thr Ala Thr Ser
            675                 680                 685

Gln Pro Thr Val Thr Ala Thr Ala Thr Gln Pro Thr Gln Gln Pro Thr
        690                 695                 700

Thr Gln Pro Pro Ala Thr Val Gln Pro Thr Gln Glu Pro Thr Thr Ser
705                 710                 715                 720

Thr Ala Thr Asn Arg Pro Thr Ser Thr Ala Thr Asn Gly Ser Gly Gly
                725                 730                 735

Asp Gly Asp Gly Gly Gly Gly Asp Gly Asp Gly Gly Gly Gly Gly Asn
            740                 745                 750

Gly Asn Asn Gly Asn Gly Ala Asn Ala Ala Pro Gly Gly Asn Gly
            755                 760                 765

<210> SEQ ID NO 12
<211> LENGTH: 297
<212> TYPE: PRT
<213> ORGANISM: Propionibacterium acidi-propionici

<400> SEQUENCE: 12

Met Val Ser Ser Thr Pro Pro Ala Glu Val Asp Ile Thr Val Asp Leu
1               5                   10                  15

Val His Ala Leu Leu Ala Glu Gln His Pro Asp Leu Ala Asp Arg Arg
            20                  25                  30

Leu Lys Val Val Ala Asn Gly Trp Asp Asn Val Ile Val Arg Ile Gly
        35                  40                  45

Glu Asp Leu Val Ala Arg Leu Pro Arg Arg Gln Leu Ala Ala Asp Leu
    50                  55                  60

Ile Leu His Glu Gln Arg Trp Leu Pro Glu Leu Ala Arg Gly Leu Pro
65                  70                  75                  80

Ile Leu Val Pro Ala Pro Val Arg Gln Gly Arg Pro Gly His Gly Tyr
                85                  90                  95

Pro Trp Phe Trp Ser Ile Cys Pro Trp Phe Glu Gly Glu Val Ala Ala
            100                 105                 110

Asp Val Pro Leu Ala Asp Pro Val Arg Glu Ala Asp Arg Leu Gly Ala
        115                 120                 125

Phe Val His Ala Phe His Arg Pro Ala Pro Pro Asp Ala Pro Ser Asn
    130                 135                 140

Pro Phe Arg Asp Ile Pro Val Ala Arg Leu Ala Pro Thr Arg Gly
145                 150                 155                 160

Asn Leu Glu Gln Leu Gly Pro Gly His Glu Ser Val Ala Ala Leu Ile
                165                 170                 175

Asp Arg Leu Ala Ala Val Pro Ala Trp Asp Ser Pro Val Trp Val
            180                 185                 190

His Gly Asp Leu His Ala Ala Asn Leu Leu Val Ala Asp Gly Arg Ile
        195                 200                 205

Cys Ala Val Leu Asp Phe Gly Asp Leu Thr Ala Gly Asp Pro Ala Val
    210                 215                 220

Asp Leu Ala Val Ala Trp Met Leu Phe Asp Ala Asp Arg Arg
225                 230                 235                 240

Phe Arg Ile Ala Ala Gly Gly Ala Pro Val Asp Asp Ala Thr Trp
                245                 250                 255

Asp Arg Ala Arg Leu Trp Gly Leu His Leu Gly Leu Ile Phe Leu Leu
            260                 265                 270
```

```
His Ser Glu Asp Ser Glu Gln Phe Ser Arg Leu Gly Ala Arg Leu Phe
        275                 280                 285

Arg Ala Val Thr Ser Glu Asp Ala Gly
    290                 295

<210> SEQ ID NO 13
<211> LENGTH: 260
<212> TYPE: PRT
<213> ORGANISM: Propionibacterium acidi-propionici

<400> SEQUENCE: 13

Met Thr Arg Thr Met Thr Leu Pro Asp Gly Arg Thr Met Ala Trp Glu
1               5                   10                  15

Glu Tyr Gly Ala Ala Asp Gly Arg Pro Val Leu Phe Leu His Gly Thr
            20                  25                  30

Pro Gly Gly Arg Leu Ser Ala Ala Lys Tyr Glu Pro Phe Ala Leu Ala
        35                  40                  45

Arg Gly Leu Arg Leu Val Ala Pro Asp Arg Pro Gly Tyr Gly Leu Ser
    50                  55                  60

Thr Ala Arg Pro Gly Met Thr Leu Ser Asp Tyr Ala Glu Ala Leu Leu
65                  70                  75                  80

Asp Leu Cys Trp Trp Arg Gly Trp Gly Pro Val Pro Val Val Ala Gly
                85                  90                  95

Ser Ala Gly Ala Ala Tyr Ala Leu Ala Leu Gly Ala Ala Ala Ser Glu
            100                 105                 110

Met Val Thr Gly Val Ser Ile Phe Ser Gly Ile Ala Pro Met Thr Asp
        115                 120                 125

Asp Glu Ala Arg Thr Leu Ile Pro Val Asn Gln Gln Leu Arg Cys Ala
    130                 135                 140

Val Asp Asp Pro Ala Glu Leu Gln Arg Leu Val Gly Gln Val Arg Asp
145                 150                 155                 160

Ala Ile Leu Ala Gly Thr Leu Lys Gly Leu Pro Glu Asp Pro Ala Leu
                165                 170                 175

Thr Asp Ala Leu Lys Pro Gly Ala Asp Gly Met Val Ala Asp Tyr Arg
            180                 185                 190

Asn Val Phe Gly Glu Trp Gly Pro Asp Pro Val Ala Val Arg Val Pro
        195                 200                 205

Val Leu Trp Ile His Gly Thr Asp Asp Val Asn Ala Pro Ile Ser Ala
    210                 215                 220

Ala Arg Arg Leu Ala Ser Gln Leu Pro Glu Ala Arg Phe Glu Glu Val
225                 230                 235                 240

Ser Gly Gly Val His Ala Pro Ser Ala Glu Thr Leu Glu Arg Val Phe
                245                 250                 255

Asp Ala Thr Pro
            260

<210> SEQ ID NO 14
<211> LENGTH: 249
<212> TYPE: PRT
<213> ORGANISM: Propionibacterium acidi-propionici

<400> SEQUENCE: 14

Met Gln Tyr Thr Leu Ile Asp Gly Leu Gln Lys Leu Leu Ser Lys Ala
1               5                   10                  15

Leu Ser Val Leu Ala Ala Trp Leu Leu Val Arg Ile Ile Asp His Gly
            20                  25                  30
```

```
Gly Phe Arg Asp Leu Ala Leu Ser Val Gly Trp Ser Arg Gly Leu Met
            35                  40                  45

Gly Ser Leu Ile Ala Leu Ile Val Gly Leu Val Ser Gly Ile Ala
 50                  55                  60

Ile Leu Ala Gly Asp Gly Ile Gly Leu Leu Ser Asn Thr Gly Phe Gly
 65                  70                  75                  80

Glu Ser Phe His Glu Gln Ser Val Thr Leu Leu Ile Leu Ser Ile Val
                 85                  90                  95

Leu Ser Ile Val Phe Ala Ala Ile Tyr Ala Val Gly Met Asn Thr Leu
                100                 105                 110

Trp Phe Gly Tyr Leu Leu Arg Ser Leu Ser Gly Arg Pro Val Ile Gly
                115                 120                 125

Val Val Val Ser Leu Val Pro Ala Leu Val Ser Leu Leu Pro Ala
            130                 135                 140

Pro Thr Ser Arg Phe Asp Pro Ser Ile Leu Ala Leu Met Ala Gln Ser
145                 150                 155                 160

Thr Pro Glu Ala Val Gly Val Gly Leu Ala Ser Ala Val Met Val Leu
                165                 170                 175

Ala Leu Arg Ser Val Trp Pro Ser Val Gly Ile Ala Val Gly Ala Arg
                180                 185                 190

Leu Ile Ser Leu Val Ser Pro Gly Ala Met Thr Ser Pro Ser Ala Ala
            195                 200                 205

Thr Ala Val Ser Gln Ser Ala Ile Thr Gly Ala Leu Phe Ala Val Ala
210                 215                 220

Ala Leu Val Thr Ala Leu Leu Met Gly Arg His Arg Trp Gln Gln Val
225                 230                 235                 240

Ala His Val Gly Pro Phe Ala Thr Thr
                245

<210> SEQ ID NO 15
<211> LENGTH: 396
<212> TYPE: PRT
<213> ORGANISM: Propionibacterium acidi-propionici

<400> SEQUENCE: 15

Met Glu Pro Met Gly Val Gly Val Ile Gly Thr Gly Asp Ile Ser Asp
1               5                   10                  15

Val Tyr Leu Ala Asn Leu Asn Lys Tyr Pro Gly Phe Val Arg Leu Val
                20                  25                  30

Ala Cys Gln Asn Arg Thr Arg Ala Lys Ala Glu Arg Gln Ala Ala Arg
            35                  40                  45

Tyr Gly Ile Gly Arg Val His Asp Thr Val Glu Glu Leu Leu Ala Asp
 50                  55                  60

Pro Glu Val Lys Leu Val Leu Asn Leu Thr Thr Pro Glu Ala His Ala
 65                  70                  75                  80

Pro Ile Asn Met Ala Ala Leu Ser Ala Gly Arg His Val Tyr Ser Glu
                 85                  90                  95

Lys Pro Leu Ala Thr Ser Leu Glu Asp Ala Arg Arg Thr Leu Asp His
                100                 105                 110

Ala His Asp Leu Gly Leu His Leu Gly Cys Ala Pro Asp Thr Trp Leu
            115                 120                 125

Gly Gly Arg Ala Gln Thr Met Arg Asp Leu Ile Asp Ser Gly Glu Ile
        130                 135                 140

Gly Glu Val Thr Ala Gly Val Ala Thr Ile Val Tyr Pro Gly Leu Glu
145                 150                 155                 160
```

```
Trp Phe His Pro Ser Pro Phe Gln Ser Tyr Arg Ala Asp Val Gly Pro
                165                 170                 175

Leu Ala Asp Ile Gly Ile Tyr Tyr Val Ser Met Leu Val Ala Leu Leu
            180                 185                 190

Gly Pro Val Arg Gln Val Ala Ala Met Gly Lys Lys Thr Phe Asp Glu
        195                 200                 205

Arg Thr Ala His Tyr Gly Pro Ile Ala Gly Arg Pro Ile Pro Val Glu
    210                 215                 220

Val Glu Thr His Val Ser Ala Ser Leu Glu Phe Glu Gln Gly Ala Val
225                 230                 235                 240

Val Thr Leu Leu Val Ser Thr Asp Val Pro Asp Ser Gln Leu Pro Arg
                245                 250                 255

Met Glu Leu Tyr Gly Thr Arg Gly Thr Leu Cys Met Pro Glu Thr Glu
            260                 265                 270

Pro Met Ala Gly Pro Asn Thr Phe Gly Gly Pro Leu Trp Ile Arg Thr
        275                 280                 285

Leu Asp Asp Ala Arg Tyr Lys Asp Ile Pro Arg Pro Ala Pro Thr Pro
    290                 295                 300

Trp Thr Glu Ala Glu Asn Arg His Arg Phe Asn Glu Thr Asp Phe Gly
305                 310                 315                 320

Ala Asp Pro Ser Val Pro Arg Ile Asn Ser Arg Gly Ile Gly Leu Val
                325                 330                 335

Asp Glu Val Leu Ala Ile Ala Glu Gly Arg Pro Met Arg Cys Ser Gly
            340                 345                 350

Asp Leu Ala Cys His Val Leu Asp Val Ile Glu Ser Ile Tyr Ala Ser
        355                 360                 365

Ser Arg Gln Arg Arg Phe Val Glu Val Ala Ser Ser Cys Arg Arg Pro
    370                 375                 380

Ala Pro Leu Pro Ala Asp Phe Pro Gly Pro Gln Val
385                 390                 395

<210> SEQ ID NO 16
<211> LENGTH: 311
<212> TYPE: PRT
<213> ORGANISM: Propionibacterium acidi-propionici

<400> SEQUENCE: 16

Met Ala Leu Asn Glu Val Thr Phe Pro Ser His Asp Gly Arg Asp Gln
1               5                   10                  15

Ile His Gly Trp Ile Tyr Ser Pro Val Arg Pro Val Arg Gly Ile Val
            20                  25                  30

Gln Ile Ala His Gly Leu Gly Glu His Ser Arg Arg Tyr Leu His Met
        35                  40                  45

Ile Thr Thr Leu Leu Asp Ala Gly Phe Val Val Ala Ala Asp Asp His
    50                  55                  60

Ala Gly His Gly Ala Thr Ala Met Ala Ser Gly Val Trp Gln Asp Thr
65                  70                  75                  80

Gly Pro His Gly Val Asp Thr Val Leu Ile Asp Glu Arg Thr Leu His
                85                  90                  95

Asp Leu Ala Val Glu Leu His Pro Asp Leu Pro Phe Val Phe Phe Gly
            100                 105                 110

His Ser Trp Gly Ser Met Ile Ala Arg Gly Tyr Ala Ser Arg Tyr Pro
        115                 120                 125

Asp Asp Leu Ser Ala Leu Val Leu Cys Gly Ile Ala Ala Gly Met His
    130                 135                 140
```

```
Gly Ile Glu Glu Thr Leu Asp Arg Asp Ala Leu Ala Ala Ala Ile Ala
145                 150                 155                 160

Glu Gly Asp Gly Ser Gly Pro Asp Thr Gly Phe Gln Asp Gln Met Phe
                165                 170                 175

Asp Gly Phe Thr Ser Arg Cys Gly Pro Asp Ala Gly Pro Thr Ala Trp
            180                 185                 190

Val Ala Ala Asp Pro Gln Val Ala Asp His Gly Ile Asp Pro Leu
        195                 200                 205

Asn Asn Phe Gly Ala Pro Met Ser Leu Arg Phe Val Arg Asp Phe Ala
    210                 215                 220

Arg Leu Tyr Asp Glu Val Asn Asp Ala Ala Trp Pro Gly Thr Val Pro
225                 230                 235                 240

Ala Thr Val Pro Val Leu Ile Leu Ala Gly Glu Gln Asp Pro Val Ala
                245                 250                 255

Asn Tyr Gly Glu Gly Ala Leu Thr Val Ala Asn Gln Leu Trp Asp Thr
            260                 265                 270

Gly His Glu Val Glu Thr Arg Ile Tyr Thr Gly Val Arg His Glu Val
        275                 280                 285

His Asn Glu Pro Ala Thr Arg Ala Gln Val Glu Ala Asp Leu Leu Ala
    290                 295                 300

Phe Val Glu Arg Val Thr Gly
305                 310

<210> SEQ ID NO 17
<211> LENGTH: 488
<212> TYPE: PRT
<213> ORGANISM: Propionibacterium acidi-propionici

<400> SEQUENCE: 17

Met Ser Ser Pro Ser Lys Thr Ser Ala Ser Pro Gln Ala Thr Gln Gly
1               5                   10                  15

Gly Ser Ala Pro Ala Pro Gln Met Lys Gly Arg His Leu Val Met Met
            20                  25                  30

Ser Leu Gly Ser Ala Ile Gly Thr Gly Leu Phe Leu Gly Ser Gly Lys
        35                  40                  45

Gly Ile Ala Ala Ala Gly Pro Ser Val Leu Val Ala Tyr Val Val Ala
50                  55                  60

Gly Leu Val Val Ile Ala Ile Met Arg Met Leu Gly Glu Met Val Ala
65                  70                  75                  80

Ala His Pro Asp Ser Gly Ala Phe Ser Val Tyr Thr Ala Arg Ala Met
                85                  90                  95

Gly Pro Ala Ala Gly Phe Ala Met Gly Trp Val Trp Val Glu Leu
            100                 105                 110

Ala Val Val Val Ala Ala Glu Gly Thr Ala Ala Ala Gln Ile Phe Leu
        115                 120                 125

Ala Val Trp Pro Ile Ala Pro Asp Trp Leu Leu Thr Leu Ile Phe Met
130                 135                 140

Val Ala Leu Thr Ala Ile Asn Leu Phe Gly Val Asp Lys Phe Gly Glu
145                 150                 155                 160

Phe Glu Phe Trp Phe Ala Leu Ile Lys Val Ala Ala Val Ala Phe
                165                 170                 175

Leu Val Ile Gly Val Leu Leu Cys Gly Val Phe Pro Ala Pro Ala
            180                 185                 190

Pro Gly Leu Ser Asn Phe Leu His His Gly Gly Phe Met Pro Asn Gly
        195                 200                 205
```

```
Trp Gly Gly Val Ala Thr Gly Leu Leu Ile Val Ile Phe Ala Phe Gly
    210                 215                 220

Gly Ile Glu Ile Val Ala Val Ala Ala Ala Glu Thr Glu Asn Pro Arg
225                 230                 235                 240

Lys His Val Gly Lys Ala Ile Asn Thr Ile Ile Trp Arg Ile Leu Val
                245                 250                 255

Phe Tyr Met Gly Ser Val Ala Ile Met Val Phe Ala Leu Pro Trp Asp
                260                 265                 270

Asp Pro Lys Leu Ala Ser Ser Pro Phe Val Ala Val Leu Asp Leu Ala
            275                 280                 285

Lys Ile Pro Gly Ala Asp Ala Val Leu Thr Leu Ile Ile Val Leu Ala
290                 295                 300

Val Leu Ser Ser Leu Asn Ala Asn Leu Tyr Gly Asp Ser Arg Met Leu
305                 310                 315                 320

Gly Ser Leu Ala Glu Arg Gly Leu Ala Pro Lys Ala Met Thr Gly Lys
                325                 330                 335

Asn Arg Arg Asn Val Pro Val Ala Ala Val Leu Ser Ser Val Ala Phe
                340                 345                 350

Gly Tyr Val Cys Val Val Leu Thr Tyr Ile Trp Gly Ala Lys Val Leu
                355                 360                 365

Asp Val Leu Leu Asn Val Val Gly Ser Val Ile Ile Val Thr Tyr Leu
            370                 375                 380

Phe Thr Ile Ala Ser Gln Ile Ile Leu Arg Arg Ala Glu Lys Thr
385                 390                 395                 400

Gly Glu Glu Leu Pro Phe Arg Met Trp Gly Tyr Pro Tyr Leu Ser Trp
                405                 410                 415

Leu Thr Leu Ala Val Leu Ile Gly Ile Ile Gly Leu Gly Met Thr Asp
                420                 425                 430

Ala Gly Val Arg Gly Gln Ile Leu Ala Thr Phe Gly Leu Thr Val Val
            435                 440                 445

Leu Phe Val Ile Gly Ile Val Arg Thr Arg Arg Leu Gly Gln Asp Pro
    450                 455                 460

Phe Lys Pro Val Val Thr Pro Gly Asp Arg Leu Val Asp Ala Asp Pro
465                 470                 475                 480

Ala Ala Glu Pro Ala Gly Thr Asp
                485

<210> SEQ ID NO 18
<211> LENGTH: 520
<212> TYPE: PRT
<213> ORGANISM: Propionibacterium acidi-propionici

<400> SEQUENCE: 18

Met Ala Pro Arg Pro Thr Ser Thr Asp Ala Pro Asp Asp Ser Ala Ala
1               5                   10                  15

Ser Asp Glu Glu Glu Val Val Glu Leu Gly Thr Gly Arg Arg Ile Thr
                20                  25                  30

Glu Pro Leu Arg Ala Pro Thr Ala Gly Ile Pro Ala His Ala Pro Arg
            35                  40                  45

Val Val Glu Met Gly Ala Glu Thr Val Pro Leu Arg Ala Pro Gly Val
        50                  55                  60

Ala Ala Leu Val Glu Glu Leu Gly Leu Thr Ala Ser Met Thr His Pro
65                  70                  75                  80

Arg Pro Gly Pro Ala Leu Leu Ser Ser Arg Arg Gly Ala Val Pro Met
                85                  90                  95
```

```
Pro Asp Gly Val Thr Pro Thr Gly Pro Thr Arg Leu Leu Pro Thr Val
            100                 105                 110

Arg Ser Gln Ile Leu Ser Pro Ser Gly Leu Leu Arg Ala Ala Ala Glu
            115                 120                 125

Pro Ile Thr Gly Arg Arg His Ile Asp Gly Asp Val Ser Val Gly Glu
            130                 135                 140

Phe Ile Glu Thr Arg Phe Gly Pro Gln Val Ala Arg Ala Val Val Asp
145                 150                 155                 160

Pro Leu Leu Gly Ala Ile His Ala Ala Asp Ile Asn Arg Phe Ser Leu
            165                 170                 175

Ala Ala Ala Ala Pro Ala Leu Val Glu Thr Ala Ala Glu Gly Asp Ser
            180                 185                 190

Met Leu Leu Gly Thr Leu Gly Arg Glu Ala Arg Arg Ala Ala Gly Trp
            195                 200                 205

Ala Arg Gly Leu Pro Leu Arg Gly Tyr His Arg Met Ile Arg Met Met
            210                 215                 220

Gly Leu Gln Glu Glu Asp Leu Asp Arg Gln Ala Pro Ala Pro Ser Leu
225                 230                 235                 240

Ala Ser Trp Pro Arg Gly Thr Ala Thr Leu Ala Asp Arg Leu Ala Ala
            245                 250                 255

Ser Val Arg Ala Arg Gly Thr Leu Leu Leu Asn Thr Arg Ala Thr Arg
            260                 265                 270

Leu Thr Pro Pro Asn Asp Gly Gly Thr Ala Trp Arg Val Gly Val Glu
            275                 280                 285

Gly Leu Asp Gly Ala Arg Glu Leu Thr Ala Asp Ala Val Val Val Ala
            290                 295                 300

Thr Gly Ser Ala Ser Ala Ala Gly Met Leu Ala Asp Val Ser Pro Arg
305                 310                 315                 320

Ala Ala Glu Ile Leu Ala Gly Leu Arg Ala Val Ser Val Ala Thr Val
            325                 330                 335

Ile Leu Asp Leu Pro Leu Asp Glu Thr Leu Ala Ala His Pro Leu Ser
            340                 345                 350

Gly Ala Ala Thr Trp Phe Ile Gly Ser Gly Trp Ser Pro Leu Ile Arg
            355                 360                 365

Gln Val Thr Asn Leu Ser His Lys Trp Pro Thr Thr Leu Gly Gly Asp
            370                 375                 380

Arg Leu Val Leu Arg Val Ser Ala Gly Arg Asp Gly Gly Arg Pro Leu
385                 390                 395                 400

Asp Ala Met Thr Asp Asp Leu Ala Arg Ala Val Val Ala Glu Leu
            405                 410                 415

Arg Arg Leu Gly Leu Pro Val Ala Ala Pro Ala Glu Ala Val Thr Val
            420                 425                 430

Pro Ser Lys Asp Ala Arg Arg Met Cys Thr Leu Val Ala Arg Phe
            435                 440                 445

Pro Asn Ala Met Pro Gln Pro Ala Pro Gly His Arg Gly Arg Met Glu
            450                 455                 460

Ser Leu Ala Ala Ala Leu Ser Glu Val Pro Gly Leu Gly Leu Gly Gly
465                 470                 475                 480

Cys Ala Thr Asp Gly Ala Gly Val Gly Thr Ala Ile Leu Ala Gly Arg
            485                 490                 495
```

Arg Leu Ala Arg Gln Ile Ser Ala Phe Leu Asp Arg Asp Pro Arg Asp
            500                 505                 510

Pro Arg Glu Gln Gly Gly Thr Leu
        515                 520

<210> SEQ ID NO 19
<211> LENGTH: 256
<212> TYPE: PRT
<213> ORGANISM: Propionibacterium acidi-propionici

<400> SEQUENCE: 19

Met Leu Val Ser Glu Val Met Ser Gln Gln Thr Pro Met Ser Arg Val
1               5                   10                  15

Val Gly Pro Trp Thr Glu Trp Met Gly Arg Trp Pro Thr Pro Asp Asp
            20                  25                  30

Leu Ala Glu Glu Ala Gly Ala Ala Val Ala Ala Trp Gly Arg Leu
        35                  40                  45

Gly Tyr Pro Arg Arg Ala Leu Arg Leu His Ala Ala Val Ala Ile
    50                  55                  60

Ala Glu Arg Phe Asp Gly Val Val Pro Ser Thr Tyr Ala Glu Leu Ile
65                  70                  75                  80

Glu Leu Pro Gly Ile Gly Asp Tyr Thr Ala Ala Val Val Ser Phe
                85                  90                  95

Ala Phe Gly Gly Arg Ala Ala Val Leu Asp Thr Asn Val Arg Arg Val
            100                 105                 110

Leu Ala Arg Val Glu Thr Gly Val Ala Asn Cys Gly Ser Ala Thr Ser
        115                 120                 125

Arg Ala Asp Arg Asp Leu Ala Ala Lys Trp Leu Pro Glu Ser Asp Asp
    130                 135                 140

Asp Ala Ala Arg Trp Ala Val Ser Ser Met Glu Leu Gly Ala Leu Val
145                 150                 155                 160

Cys Val Ala Arg Ala Pro Leu Cys Glu Ser Cys Pro Val Ala Gly His
                165                 170                 175

Cys Arg Trp Leu Glu Ala Gly Lys Pro Thr Asp Gly Ala Pro Val Arg
            180                 185                 190

Arg Gly Gln Ala Trp Lys Gly Thr Asp Arg Gln Cys Arg Gly Val Ile
        195                 200                 205

Leu Asp Leu Val Arg Asn Ser Ala Gly Val Glu Val Glu Val Ala
    210                 215                 220

Leu Glu Ala Trp Pro Lys Arg His Gln Ala Glu Lys Cys Leu Gly Thr
225                 230                 235                 240

Leu Leu Asp Asp Gly Leu Ile His Arg Glu Gly Ser Val Leu Arg Leu
                245                 250                 255

<210> SEQ ID NO 20
<211> LENGTH: 627
<212> TYPE: PRT
<213> ORGANISM: Propionibacterium acidi-propionici

<400> SEQUENCE: 20

Met Thr Val Val Leu Ile Ile Val Ile Ala Ala Leu Phe Ile Val Ala
1               5                   10                  15

Ala Ala Glu Leu Leu Ala Asp Arg Thr Gly Ile Ala Ala Pro Ile Leu
            20                  25                  30

Leu Leu Leu Leu Gly Ala Gly Val Ala Leu Ile Pro Gly Met Pro Glu
        35                  40                  45

-continued

```
Val Glu Val Glu Pro Glu Leu Val Leu Met Ile Ile Leu Pro Pro Leu
 50                  55                  60

Leu Tyr Ser Ser Ala Val Asn Met Pro Val Ala Asp Phe Arg Arg Asn
 65                  70                  75                  80

Leu Ala Pro Ile Ser Val Leu Ala Val Ala Leu Val Ala Val Ser Ala
                 85                  90                  95

Ala Val Ile Gly Phe Ile Val Asn Gln Met Val Pro Gly Ile Gly Ile
                100                 105                 110

Ala Ala Cys Val Ala Leu Gly Ala Ile Val Ser Pro Thr Asp Ala Val
                115                 120                 125

Ala Thr Ser Ile Val Lys Lys Ala Gly Val Ser Arg Arg Leu Val Thr
    130                 135                 140

Val Leu Asp Gly Glu Gly Leu Ile Asn Asp Ala Ser Ala Leu Val Ile
145                 150                 155                 160

Leu Ser Ser Ala Val Gly Ala Met Phe Ala Glu Ile Ser Ala Gly Glu
                165                 170                 175

Val Ile Leu Asp Phe Val Leu Ala Val Val Ala Val Val Val Val Gly
                180                 185                 190

Trp Leu Val Gly His Ala Met Ile Trp Ile Arg Ala Arg Ile His Glu
    195                 200                 205

Ala Thr Pro Asp Thr Val Leu Ser Met Ala Thr Pro Phe Leu Ala Phe
    210                 215                 220

Leu Pro Ala Glu His Leu His Gly Ser Gly Leu Val Ala Ala Val Ala
225                 230                 235                 240

Ala Gly Leu Val Ala Ser His Gln Gly Pro Arg Val Leu Thr Pro Thr
                245                 250                 255

Gln Arg Met Ser Ser Arg Thr Thr Trp Arg Ser Leu Met Leu Ile Leu
                260                 265                 270

Glu Ser Ala Val Phe Leu Leu Met Gly Leu Glu Leu Thr Ala Val Val
                275                 280                 285

Glu Asp Met Glu Ala Glu Ser Phe Gly Trp Lys Leu Ala Val Ala Val
    290                 295                 300

Ala Ala Val Ala Leu Val Met Thr Met Val Leu Arg Thr Val Val Val
305                 310                 315                 320

Thr Pro Leu Leu Met Trp Val Thr Arg Arg Ser Lys Arg Arg Ser Lys
                325                 330                 335

His Arg Ser Tyr Leu Glu Lys Ala Ser Gln Lys Val Ala Asp Ala Leu
                340                 345                 350

Glu Ser Asp Glu Glu Ile Thr Ile Arg Gly Asn Thr Ile Asp Ala Asp
    355                 360                 365

His Ala Ala Arg Phe Arg His Arg Ile Val Arg Thr Ile Ser Asp Leu
    370                 375                 380

Asp Tyr Tyr Ile Lys His Pro Leu Gly Pro Arg Glu Gly Ser Val Met
385                 390                 395                 400

Ile Trp Ala Gly Met Arg Gly Ala Ile Thr Leu Ala Ala Ala Gln Thr
                405                 410                 415

Leu Pro Leu Asp Thr Pro His Arg Ser Phe Leu Val Phe Val Ala Phe
                420                 425                 430

Leu Val Ala Ala Ala Ser Leu Leu Ile Gln Gly Ser Thr Leu Gly Leu
                435                 440                 445

Val Val Lys Val Ala Lys Pro Ala Thr Ser Glu Gly Val Asp Pro Asp
    450                 455                 460
```

Glu Gln Ala Glu Ile Arg Lys Leu Met His Arg Ala Ala Arg Lys Val
465                 470                 475                 480

Pro Val Pro Ala Pro Met Arg Arg Leu Leu Ala Arg Thr Gly His Gln
                485                 490                 495

Glu Ser Glu Asp Val Glu Glu Asn Arg Ala Gln Ala Ala Ala Val Ala
            500                 505                 510

Leu Ala Trp Arg Gln Phe Ala Ala Leu Arg Asp Arg Gly Val Glu Ser
        515                 520                 525

Glu Ala Pro Ala Glu Ala Gly Pro Glu Arg Leu Gly Glu Thr Ala Pro
530                 535                 540

Ile Pro Arg Ile Val Gly Lys Gln Leu Pro Gly Glu Asp Ala Arg Ala
545                 550                 555                 560

Lys Val Leu Ala Ser Pro Glu His Arg Arg Ala Ala Glu Ile Ser
                565                 570                 575

Arg Gln Tyr Ala Leu Arg Leu Ile Val Ala Gln Arg Lys Val Leu Leu
                580                 585                 590

Asp Ala Asn Asp Ala Gly Arg Phe Ser Pro Glu Ala Val Ser Ser Ala
                595                 600                 605

Leu Asp Thr Leu Asp Ala Asp Gln Leu Ser Leu Glu Ala Arg Gly Thr
610                 615                 620

Ser Leu Asp
625

<210> SEQ ID NO 21

<400> SEQUENCE: 21

000

<210> SEQ ID NO 22
<211> LENGTH: 540
<212> TYPE: PRT
<213> ORGANISM: Propionibacterium acidi-propionici

<400> SEQUENCE: 22

Met Ser Ile Leu Arg Thr Lys Ser Val Glu Gln Ser Leu Arg Asp Thr
1               5                   10                  15

Glu Asp Pro Glu His Gln Leu Lys Lys Ser Leu Ser Trp Val Glu Leu
                20                  25                  30

Thr Met Phe Gly Ile Gly Val Val Ile Gly Ala Gly Ile Phe Thr Met
            35                  40                  45

Thr Gly Arg Val Ala His Ser Met Thr Gly Pro Ser Ile Ile Ile Ser
        50                  55                  60

Phe Ile Val Ala Ala Ile Ala Cys Gly Leu Ala Ala Met Cys Tyr Ala
65                  70                  75                  80

Glu Phe Ala Ser Thr Val Pro Val Ala Gly Ser Ala Tyr Thr Phe Ser
                85                  90                  95

Tyr Ala Ser Met Gly Glu Ile Phe Ala Trp Ile Ile Gly Trp Asp Leu
                100                 105                 110

Phe Leu Glu Leu Phe Leu Ala Ser Val Val Ala Gln Gly Trp Ser
            115                 120                 125

Ala Tyr Leu Ala Val Phe Leu Ser Gln Leu Gly Ile Asp Leu Pro Pro
        130                 135                 140

Gln Ile Val Ser Gly Gly Arg Phe Asp Leu Leu Ala Phe Gly Leu Ile
145                 150                 155                 160

```
Met Val Leu Gly Met Leu Leu Ile Gly Gly Ile Lys Glu Ser Val Arg
            165                 170                 175
Val Asn Thr Val Leu Val Ala Ile Lys Leu Phe Ile Val Met Phe Val
        180                 185                 190
Ile Phe Ala Gly Ile Gly Tyr Val Lys Ala Ser Asn Phe Thr Pro Phe
            195                 200                 205
Val Pro Asp Lys Gln Pro Val Glu Ser Thr Gly Gly Leu Thr Gln Pro
    210                 215                 220
Leu Leu Gln Trp Phe Thr Gly Ser Gly Gln Thr Ala Phe Gly Val Ser
225                 230                 235                 240
Gly Ile Val Ala Gly Ala Ala Leu Val Phe Phe Ala Tyr Ile Gly Phe
                245                 250                 255
Asp Val Val Ala Thr Thr Ala Glu Glu Ala Lys Asn Pro Lys Arg Asp
            260                 265                 270
Val Pro Leu Gly Ile Leu Gly Ser Leu Val Val Cys Thr Ile Leu Tyr
        275                 280                 285
Ile Ala Ile Ser Leu Val Leu Ile Gly Met Val Pro Tyr Asp Gln Leu
    290                 295                 300
Asp Pro Ser Ala Ser Leu Ala Lys Ala Phe Thr Thr Val Gly Lys Pro
305                 310                 315                 320
Trp Met Ala Ile Ile Ile Ser Ala Gly Ala Val Ala Gly Leu Thr Thr
                325                 330                 335
Val Val Leu Thr Met Met Ile Gly Ala Thr Arg Val Ile Phe Ala Met
            340                 345                 350
Ser Arg Asp Gly Leu Leu Pro Glu Gly Leu Ser His Val His Pro Lys
        355                 360                 365
Thr Arg Thr Pro Tyr Arg Ile Thr Leu Ile Ile Met Leu Ala Asp Gly
    370                 375                 380
Leu Leu Ala Ala Leu Val Pro Pro Gly Ile Leu Asp Glu Met Val Asn
385                 390                 395                 400
Ile Gly Thr Leu Leu Ala Phe Val Met Val Ser Val Gly Ile Ile Val
                405                 410                 415
Leu Arg Arg Lys Arg Pro Asp Leu Pro Arg Ala Phe Val Pro Trp
            420                 425                 430
Val Pro Val Pro Ile Val Ser Ala Ile Ile Cys Leu Tyr Leu Met
        435                 440                 445
Leu Asn Leu Ser Ile Glu Thr Trp Met Arg Phe Leu Ile Trp Met Val
    450                 455                 460
Ile Gly Ile Val Val Tyr Phe Thr Tyr Ser Lys Asn His Ser Arg Leu
465                 470                 475                 480
Ala His Gly Ser Glu Leu Thr Ala Asp Ile Asn Ala Glu Ile Thr Asn
                485                 490                 495
Val Met Gly His Gln Tyr Asp Ala Arg Arg Gly Ser Arg Arg Ala Gly
            500                 505                 510
Ser Pro Ala Ala Gln Ala Ser Ser Ala Gly Ser Ala Glu Pro Ala Asp
        515                 520                 525
Ala Ala Pro Glu Leu Ser Asp Pro Pro Lys Glu Ser
    530                 535                 540

<210> SEQ ID NO 23
<211> LENGTH: 674
<212> TYPE: PRT
<213> ORGANISM: Propionibacterium acidi-propionici
```

<400> SEQUENCE: 23

```
Met Arg Asp Ala Met Arg Ala Thr Val Pro Ala Leu Ala Leu Ala Val
1               5                   10                  15

Ala Leu Ser Ala Cys Ser Gly Ser Gly Gln Ser Arg Gly Ser Ala Ser
            20                  25                  30

Ala Ser Gly Asp Gly Val Ala Ser Leu Thr Glu Thr Lys Val Thr Pro
        35                  40                  45

Leu Val Ser Ser Ile Gly Ser Arg Asp Gly Ala Asp Leu Lys Pro Val
    50                  55                  60

Arg Leu Ala Asp Gly Leu Thr Pro Pro Thr Asn Arg Trp Phe Ser Gly
65                  70                  75                  80

Met Ala Tyr Gly Ser Thr Ala Gln Pro Val Phe Pro Leu Pro Leu Ser
                85                  90                  95

Phe Ser Leu Leu Gly Ser Gly Phe Ala Leu Gly Leu Pro Asp Ile Lys
            100                 105                 110

Thr Ser Asp Arg Thr Ile Met Gly Gly Asn Arg Pro Ala Val Gln Ile
            115                 120                 125

Gly Ala Gly Ala Asp Ser Trp Lys Ile Thr Arg Tyr Asp Glu Met Ser
130                 135                 140

Val Thr Leu Thr Gly Ser Ala Gly Gly Thr Glu Ile Gly Thr Val Thr
145                 150                 155                 160

Ile Ala Arg Gly Ser Pro Phe Val Thr Phe Arg Ala Ser Gly Arg Arg
                165                 170                 175

Thr Leu Thr Thr Asn Leu Pro Phe Thr Gly Ser Gly Ser Pro Trp Ser
            180                 185                 190

Leu Gln Ala Gly Glu Asp Arg Tyr Asp Leu Thr Gly Ser Lys Gly Val
        195                 200                 205

Ser Val Ser Gly Gly Ala Val Thr Val Pro Asp Gly Gly His Val Thr
    210                 215                 220

Leu Tyr Pro Glu Pro Glu Gly Gly Asp Ala Ala Leu Ala Arg Leu
225                 230                 235                 240

Ala Ala Ser Pro Leu Arg Ser Thr Ala Ser Ser Tyr Arg Leu Ser Gly
                245                 250                 255

Ser Thr Ala Thr Thr Arg Leu Ala Tyr Ser Thr Asp Gly Ser Pro
            260                 265                 270

Thr Ala Ile Ala Ala Leu Pro His Gln Gln Ala Gly Leu Ala Thr Gly
        275                 280                 285

Gln His Cys Asp Leu Gly Ser Tyr Arg Ser Val Leu Gly Thr Met Lys
    290                 295                 300

Leu Cys Arg Gly Thr Ala Leu Ser Trp Asp Thr Lys Thr Arg Pro Ala
305                 310                 315                 320

Thr Ala Gln Leu Asp Leu Ser Gly Leu Ala Asp Gln Arg Ala Ala
                325                 330                 335

Leu Arg Thr Gln Val Asp Ala Asp Val Arg Ala Leu Lys Pro Tyr Pro
            340                 345                 350

Ala Asp Thr Tyr Phe Gly Gly Lys Ala Leu Tyr Arg Asp Ala Gln Leu
        355                 360                 365

Tyr Thr Leu Ala Lys Gln Val Gly Ala Ser Ser Ala Thr Thr Leu
    370                 375                 380

Lys Ser Arg Ile Val Glu Gln Leu Thr Lys Trp Ala Asp Pro Ser Gly
385                 390                 395                 400

Cys Gly Ser Arg Thr Ser Leu Cys Phe Tyr Tyr Asp Arg Ser Asn Lys
                405                 410                 415
```

```
Gly Met Val Gly Leu Thr His Ser Phe Gly Ser Glu Gln Phe Asn Asp
            420                 425                 430

His His Phe His Tyr Gly Tyr Phe Leu Tyr Ala Ala Gly Val Met Ala
            435                 440                 445

Ala Asp Asp Pro Ser Leu Val Lys Arg Trp Lys Pro Val Met Thr Leu
        450                 455                 460

Leu Ala Ala Asp Ile Ala Ser Pro Thr Asp Thr Gly Thr Phe Pro Gln
465                 470                 475                 480

Arg Arg Thr Phe Asp Pro Tyr Ser Ser His Ser Trp Ala Ser Gly Val
                    485                 490                 495

Ser Pro Phe Gly Asp Gly Asn Asn Gln Glu Ser Ala Ser Glu Ala Val
            500                 505                 510

Asn Ala Trp Val Gly Leu Gly Val Trp Ala Arg Ala Ala Gly Asp Pro
        515                 520                 525

Gln Leu Ala Ala Glu Gly Thr Trp Met Gln Ala Leu Glu Ser Asp Ser
        530                 535                 540

Gln Leu Ala Tyr Trp Thr Asn Phe Asp Thr Asp Pro Val Tyr Lys
545                 550                 555                 560

Gly Phe Gly His Ser Ile Thr Pro Leu Val Trp Gly Gly Lys Arg Asp
                    565                 570                 575

Tyr Ala Thr Trp Phe Ser Pro Glu Pro Ala Ala Ala Leu Ala Ile Leu
            580                 585                 590

Leu Ile Pro Met Asn Pro Ala Ser Gly Tyr Leu Gly Thr Asp Pro Lys
        595                 600                 605

Arg Val Ala Thr Asn Leu Lys Glu Ala Met Gly Thr Arg Gly Tyr Arg
610                 615                 620

Gln Thr Tyr Gly Asp Leu Leu Leu Tyr Ser Ala Leu Gln Gly Ser
625                 630                 635                 640

Ser Gln Arg Asp Ala Ala Val Lys Gln Val Ala Ser Leu Thr Ser Ile
                    645                 650                 655

Asp Asp Ser Leu Thr Arg Ser Tyr Ile Leu Ala Tyr Leu Tyr Ala Leu
            660                 665                 670

Lys Phe

<210> SEQ ID NO 24
<211> LENGTH: 425
<212> TYPE: PRT
<213> ORGANISM: Propionibacterium acidi-propionici

<400> SEQUENCE: 24

Met Thr Ser Pro Ala Arg Ala His Val Asp Asp Val Ile Ser Phe Val
1               5                   10                  15

Glu Ser Ser Pro Thr Ser Tyr His Ala Ala Ala Glu Leu Ala Arg Arg
                20                  25                  30

Leu Glu Glu Ala Gly Phe Glu Arg Leu Asp Glu Thr Ala Asp Trp Ser
            35                  40                  45

Gly Ala Ala Ser Val Glu Gly Arg Arg Phe Val Val Arg Asp Gly Ala
        50                  55                  60

Val Ile Ala Trp Ala Thr Pro Glu Thr Ile Gly Pro Arg Ala Gly Phe
65                  70                  75                  80

Arg Ile Val Gly Ser His Thr Asp Ser Pro Ser Phe Lys Leu Lys Pro
                    85                  90                  95

His Ala Thr Phe Thr Asn Leu Gly Trp Gln Gln Val Gly Met Glu Val
            100                 105                 110
```

Tyr Gly Gly Gly Leu Leu Asn Ser Trp Leu Asp Arg Asp Leu Gly Leu
            115                 120                 125

Ala Gly Arg Leu Val Thr Leu Asp Gly Glu Thr His Leu Val Arg Thr
130                 135                 140

Gly Pro Ile Leu Arg Ile Ser Gln Leu Ala Pro His Leu Asp Arg Thr
145                 150                 155                 160

Val Asn Gln Asp Leu Thr Leu Asp Arg Gln Arg His Leu Met Pro Ile
                165                 170                 175

Leu Ser Val Gly Arg Pro Asp Leu Asp Val Glu Asp Leu Leu Cys Glu
            180                 185                 190

Glu Ala Gly Ile Asp Arg Ser Arg Leu Gly Phe His Asp Ile Leu Ala
        195                 200                 205

Tyr Pro Thr Glu Arg Pro Ala Val Ile Gly Pro Ala Gly Glu Phe Leu
    210                 215                 220

Ala Ser Ser Arg Met Asp Asn Leu Ser Ser Val His Ser Ser Ile Ala
225                 230                 235                 240

Ala Met Val Asp Val Glu Val Gly Glu Asp Ile Ala Val Met Ala Cys
                245                 250                 255

Phe Asp His Glu Glu Val Gly Ser Ser Thr Arg Ser Gly Ala Cys Gly
            260                 265                 270

Pro Phe Leu Glu Asp Val Leu Val Arg Ile Ala Asp Gly Leu Gly Arg
        275                 280                 285

Arg Gly Asp Ala Tyr Arg Ala Met Ile Ala Arg Ser Thr Cys Ile Ser
    290                 295                 300

Ser Asp Ala Gly His Gly Val His Pro Asn Tyr Pro Glu Lys Phe Asp
305                 310                 315                 320

Pro Ala Asn His Pro Leu Leu Gly Gln Gly Pro Leu Leu Lys Ile Asn
                325                 330                 335

Ala Asn Gln Arg Tyr Ala Thr Asp Gly Val Gly Gly Ala Leu Trp Gln
            340                 345                 350

Arg Val Cys Arg Ala Ala Asp Val Pro Thr Gln Ala Phe Val Ser Asn
        355                 360                 365

Asn Ser Val Pro Cys Gly Ser Thr Ile Gly Pro Leu Thr Ala Thr Arg
    370                 375                 380

Leu Gly Met Leu Thr Val Asp Val Gly Leu Pro Leu Met Ser Met His
385                 390                 395                 400

Ser Thr Arg Glu Leu Ala Gly Val Ala Asp Leu Ser Ser Leu Ser Thr
                405                 410                 415

Ala Leu Gly Ala Phe Trp Ala Gly Ala
            420                 425

<210> SEQ ID NO 25
<211> LENGTH: 713
<212> TYPE: PRT
<213> ORGANISM: Propionibacterium acidi-propionici

<400> SEQUENCE: 25

Met Pro Ala Pro Arg Thr Ala Phe Leu Asp Leu Ser Ala Leu Ala Pro
1               5                   10                  15

Ala Lys Thr Arg Pro Ala Leu Ile Asp Ala Asp Leu Ala Arg Phe Thr
                20                  25                  30

Ala Ile Ala Glu Ala Ile Asp Ala Gln Leu Thr Thr Leu Thr Ala Gln
            35                  40                  45

Arg Arg Asp Ala Leu Ser Asp Thr Ala Arg Thr Gly Arg Ala Ala Ala
        50                  55                  60

```
Asp Arg Asp Gln Glu Val Arg Arg Ile Asn Ser Arg Ile Arg Ile Leu
 65                  70                  75                  80

Arg Asp Val Gly Pro Gln Ile Cys Leu Gly Arg Met Asp Arg Thr Gly
                 85                  90                  95

Gly Glu Pro Val Tyr Ile Gly Arg Ile Gly Leu Ser Asp Asp Ala Asp
            100                 105                 110

Arg Arg Leu Leu Val Asp Trp Arg Thr Pro Ala Ala Arg Pro Phe Phe
        115                 120                 125

Ala Ala Thr Val Ala Asp Pro Met Gly Leu Ala Gly Arg Arg Arg Phe
    130                 135                 140

Arg Trp Arg Asp Gly Arg Val Ile Asp Tyr Trp Asp Glu Ala Leu Ile
145                 150                 155                 160

Pro Asp Ala Gly Thr Asp Pro Ala Thr Met Asp Ala Glu Ser Ala Phe
                165                 170                 175

Ile Ala Ser Leu Ala Ala Ser Arg Ser Pro Arg Met Leu Asp Val Leu
            180                 185                 190

Ala Thr Ile Arg Ala Asp Gln Asp Ala Ala Val Arg Ala Glu Ala Arg
        195                 200                 205

Arg Pro Leu Ile Val Glu Gly Gly Pro Gly Thr Gly Lys Thr Val Val
    210                 215                 220

Ala Leu His Arg Ala Ala Tyr Leu Leu His Ala Asp Pro Thr Leu Asn
225                 230                 235                 240

Asn Arg Gly Gly Gly Val Leu Leu Ile Gly Pro His Pro Gly Tyr Leu
                245                 250                 255

Ala Tyr Thr Ala Asp Val Leu Pro Asp Leu Gly Glu Asp Gly Ala Arg
            260                 265                 270

Thr Ala Thr Val Ala Asp Leu Leu Pro Gln Gly Pro Asp Ala Arg Pro
        275                 280                 285

Glu Pro Asp Thr Arg Val Ala Ala Leu Lys Leu Asp Ala Arg Met Ala
    290                 295                 300

Gly Ala Val Glu Pro Ala Val Ala Leu Tyr Glu Glu Pro Pro Thr Asp
305                 310                 315                 320

Thr Leu Thr Val Asp Thr Pro Trp Gly Glu Val Ala Val Thr Ala Ala
                325                 330                 335

Ala Trp Thr Glu Ala Phe Ser Ala Ala Glu Pro Gly Ser Val His Asn
            340                 345                 350

Glu Ala Arg Asp Arg Ile Trp His Asp Leu Ile Asp Ile Leu Val Asp
        355                 360                 365

His Ala Gln Ser Leu Asp Ala Pro Glu Asp Arg Leu Arg Arg Ala Leu
    370                 375                 380

Tyr Gly Asp Glu Glu Leu Arg Glu Ala Phe Ser Arg Ala Trp Pro Ile
385                 390                 395                 400

Leu Asn Pro Glu Glu Leu Val Ala Asp Leu Trp Glu Val Pro Ala Tyr
                405                 410                 415

Leu Arg Arg Cys Ala Pro Trp Leu Thr Pro Asp Glu Ala Ala Leu Leu
            420                 425                 430

Arg Arg Gly Pro Ala His Pro Trp Thr Thr Ala Asp Leu Pro Leu Leu
        435                 440                 445

Asp Ala Ala Thr Arg Arg Leu Gly Asp Arg Arg Ala Gly Ala Ala Ala
    450                 455                 460

Arg Arg Arg Gln Ala Val Leu Ala Glu Gln Arg Ser Tyr Met Asp Asp
465                 470                 475                 480
```

Val Val Thr His Ile Leu Asp Ala Asp Asp Pro Asp Ser Ser Leu
                485                 490                 495

Ala Met Leu Arg Gly Ala Asp Leu Arg Gln Val Leu Leu Asp Thr Asp
            500                 505                 510

Ala Leu Asp Asp Gly Thr Thr Asp Pro Leu Ala Gly Pro Phe Ala His
            515                 520                 525

Ile Ile Val Asp Glu Ala Gln Glu Leu Ala Asp Ala Gln Trp Gln Met
        530                 535                 540

Leu Ile Arg Arg Cys Pro Ser Leu Ser Phe Thr Ile Val Gly Asp Arg
545                 550                 555                 560

Ala Gln Ala Arg Asp Gly Phe Pro Glu Ser Trp Glu Glu Arg Leu Gly
                565                 570                 575

Arg Leu Gly Phe His Asp Met Ser Arg Val Thr Leu Ser Val Asn Tyr
            580                 585                 590

Arg Thr Pro Ser Glu Val Met Glu Ala Ala Glu Pro Val Ile His Ala
        595                 600                 605

Ala Leu Pro Asp Ala Ala Val Pro Thr Ser Val Arg Ser Ser Gly Leu
    610                 615                 620

Pro Val Arg His Gly Arg Ile Ala His Leu Asp Arg Ile Val Ala Glu
625                 630                 635                 640

Trp Leu Asp Glu Asn Pro Glu Gly Ile Ala Ala Val Ile Gly Ala Pro
                645                 650                 655

Gly Phe Asp Gly Gly Pro Arg Val Arg Ala Leu Ser Pro Ala Asp Val
            660                 665                 670

Lys Gly Leu Glu Phe Asp Leu Val Val Ile Val Asp Pro Glu His Phe
        675                 680                 685

Gly Asp Gly Ile Thr Gly Ala Val Asp Arg Tyr Val Ala Met Thr Arg
    690                 695                 700

Thr Thr Ser Gln Leu Val Ile Leu Arg
705                 710

<210> SEQ ID NO 26
<211> LENGTH: 436
<212> TYPE: PRT
<213> ORGANISM: Propionibacterium acidi-propionici

<400> SEQUENCE: 26

Met Thr His Ser Glu Asn Leu Thr Asp Ile Ser Arg Thr Ile Asp Asp
1               5                   10                  15

Phe Asp Ser Ile Thr Asp Ala Asn Lys Ala Val Val Asp Val Met Thr
            20                  25                  30

Ala Gly Gln Pro Val Leu Val Asp Val Ala Arg Ala His Thr Leu Ile
        35                  40                  45

Pro Glu Leu Asp Thr Gly Glu Lys Val Leu Leu His Ala Gly Pro Pro
    50                  55                  60

Ile Asp Phe Glu His Met Pro Glu Thr Ile Lys Gly Ala Cys Ile Gly
65                  70                  75                  80

Ala Ala Leu Phe Glu Gly Trp Ala Ser Asp Glu Asp Ala Ala Arg Arg
                85                  90                  95

Val Val Ala Glu Gln Val Arg Leu Ile Pro Cys His His Val Gly Ala
            100                 105                 110

Val Gly Pro Met Gly Gly Ile Thr Ser Ala His Met Ala Leu Met Lys
        115                 120                 125

Val Val Asn Thr Thr Tyr Gly Asn Val Ser Tyr Ser Thr Leu Asn Glu
    130                 135                 140

-continued

Gly Ile Gly Lys Val Leu Arg Phe Gly Gly Tyr Asp Ala Glu Val Ile
145                 150                 155                 160

Asp Arg Leu Gly Trp Met Arg Asp Val Leu Gly Pro Ala Leu Ser Ser
                165                 170                 175

Ala Leu Ala Thr Thr Asp Gly Gly Tyr Pro Leu Ala Pro Val Met Ala
            180                 185                 190

Arg Ala Leu Thr Met Gly Asp Glu Met His Gln Arg Asn Ile Ala Ala
        195                 200                 205

Ser Ala Leu Phe Ala Lys Asp Met Ala Pro Leu Leu Ala Arg Ala Gly
    210                 215                 220

Leu Pro Gly Asp Thr Val Ala Glu Val Ser Asp Phe Leu Gly Arg Thr
225                 230                 235                 240

Asp Gln Phe Phe Leu Asn Val Ala Met Ala Ala Ser Lys Ala Cys Ala
                245                 250                 255

Asp Pro Ala Arg Gln Val Arg Ala Gly Ser Val Val Thr Ala Met Cys
            260                 265                 270

Arg Asn Gly Tyr Glu Phe Gly Ile Arg Val Ser Gly Leu Gly Asp Arg
        275                 280                 285

Trp Phe Thr Ala Pro Val Asn Thr Pro Ser Gly Leu Phe Phe Thr Gly
    290                 295                 300

Tyr Asp Gln Ser Gln Ala Ala Pro Asp Met Gly Asp Ser Ala Ile Met
305                 310                 315                 320

Glu Thr Phe Gly Leu Gly Gly Met Ser Ile Val Ala Ala Pro Gly Val
                325                 330                 335

Thr Pro Phe Leu Gly Ala Gly Gly Phe Ser Glu Ala Leu Ala Thr Thr
            340                 345                 350

Glu Glu Met Ala Glu Val Val Thr Ala His Asn Pro Asn Met Pro Ile
        355                 360                 365

Pro Thr Trp Asn Phe Gln Gly Ala Pro Thr Gly Ile Asp Ile Arg Leu
    370                 375                 380

Val Val Gln Thr Gly Ile Thr Pro Ile Ile Asn Ser Gly Ile Ala Ser
385                 390                 395                 400

Lys His Pro Gly Val Gly Gln Ile Gly Ala Gly Thr Val Arg Ala Pro
                405                 410                 415

Met Gly Cys Phe Thr Arg Ala Val Glu Ala Leu Ala Glu Val Tyr Gly
            420                 425                 430

Val Asp Val Ser
            435

<210> SEQ ID NO 27
<211> LENGTH: 419
<212> TYPE: PRT
<213> ORGANISM: Propionibacterium acidi-propionici

<400> SEQUENCE: 27

Met Val Cys Pro Ser Thr Leu Phe Leu Val Thr Asn Ser Tyr Pro Leu
1               5                   10                  15

Gly Thr Gly Glu Asp Phe Ile Glu Asn Glu Ile Gly Asp Leu Ala Glu
                20                  25                  30

Arg Phe Gly Arg Val Val Val Ala Val Gln Thr Arg Pro Gly Asp
            35                  40                  45

Val Ile Thr Arg Pro Val Pro Gly Asn Val Glu Val Ile Arg Ala Gly
        50                  55                  60

Gly Pro Arg Pro Ala Gly Arg Ala Ala Leu Leu Ala Ala Ala Arg Gly
65                  70                  75                  80

Leu Ala His Leu Pro Arg Gly Ser Trp Asn Arg Asp Thr Leu Arg Asp
            85                  90                  95

Pro Arg Arg Leu Gly Leu Glu Ala Met Phe Glu Glu His Ala Arg Asp
        100                 105                 110

Thr Glu Ala Asp Leu Leu Ala Gln Leu Pro Ala Leu Gly Leu Arg Pro
        115                 120                 125

Gly Ser His Ala Val Val Tyr Ser Tyr Trp Phe Leu Asp Thr Ala Arg
        130                 135                 140

Val Ala Met Leu Leu Ala Asp Leu Arg Ala Arg Gly Val Val Val
145                 150                 155                 160

Asp Arg Leu Val Ser Arg Ala His Gly Tyr Asp Leu Tyr Pro Glu Arg
                165                 170                 175

Ala Pro Tyr Gly His Leu Pro Gln Arg Glu Arg Leu Val Ala Ala Phe
        180                 185                 190

Asp Ala Val Cys Pro Val Ser Glu Gln Gly Thr Arg Thr Leu Arg Ser
        195                 200                 205

Gly Trp Pro Gly Tyr Ala Gly Lys Ile Gly Thr His His Leu Gly Thr
        210                 215                 220

Val Gly Pro Gly Ser Pro Ala Asp Cys Ser Arg Glu Pro Phe His Ile
225                 230                 235                 240

Val Ser Cys Ala Tyr Leu Val Pro Val Lys Arg Met Thr Arg Met Pro
                245                 250                 255

Gly Val Leu Ala Glu Leu Arg Gly Arg Gly Val Asp Ala Arg Trp Thr
        260                 265                 270

His Leu Gly Gly Pro Glu Ser Glu Asp Val Leu Lys Ala Ala Arg
        275                 280                 285

Asp Ala Gly Val Asp Glu Gln Val Asp Leu Gln Gly His Leu Ala His
        290                 295                 300

Glu Lys Ile Leu Glu Thr Glu Arg Gly Leu Arg Pro Ser Cys Leu Ile
305                 310                 315                 320

Asn Leu Ser Ser Ser Glu Gly Leu Pro Val Ser Met Met Glu Ala Ala
                325                 330                 335

Ser Leu Gly Ile Pro Leu Ile Gly Thr Asp Val Gly Gly Val Arg Glu
        340                 345                 350

Ile Ile Thr Asp Arg Val Asn Gly Arg Leu Ile Asn Pro Asp Phe Thr
        355                 360                 365

Asp Ser Gln Ala Ala Asp Thr Leu Gln Trp Leu Ala Asp Leu Pro Thr
370                 375                 380

Asp Asp Tyr Arg Ser Val Cys Glu Ala Ser Arg Arg Ile Trp Gln Ser
385                 390                 395                 400

Asp Tyr Asp Gln Ala Val Val Tyr Pro Arg Phe Cys Thr Glu Val Leu
                405                 410                 415

Gly Ala Asp

<210> SEQ ID NO 28
<211> LENGTH: 160
<212> TYPE: PRT
<213> ORGANISM: Propionibacterium acidi-propionici

<400> SEQUENCE: 28

Met Arg Arg Tyr Thr Ile Thr Val Ala Gly Thr Thr His Glu Ile Glu
1               5                   10                  15

Val Glu Glu Thr Ser Ala Thr Gln Phe Gln Val Arg Val Asp Gly Gln
            20                  25                  30

-continued

```
Gln Val Glu Val Glu Leu Thr Ala His Gln Asp Val Gly Asp Gln Pro
             35                  40                  45

Val Val Pro Gln Ile Asp Pro Arg His Glu Ser Ala Pro Lys Ala Pro
 50                  55                  60

Arg Val Pro Gln Gln Val Arg Thr Arg Ala Thr Gly Ser Pro Ser Pro
 65                  70                  75                  80

Ala Leu Thr Gly Gly Ala Asp Leu Ala Tyr Ser Met Thr Ala Pro Met
                 85                  90                  95

Pro Gly Val Ile Ala Ser Val Asp Ala Gly Pro Gly Asp Glu Val Ala
                100                 105                 110

Lys Gly Gln Thr Val Leu Val Leu Glu Ala Met Lys Met Lys Asn Glu
                115                 120                 125

Leu His Ala Ser Arg Ser Gly Val Ile Ala Glu Val Leu Val Ala Glu
            130                 135                 140

Gly Asp Gln Val Lys Tyr Gly Gln Thr Leu Leu Cys Phe Glu Lys Ala
145                 150                 155                 160

<210> SEQ ID NO 29
<211> LENGTH: 731
<212> TYPE: PRT
<213> ORGANISM: Propionibacterium acidi-propionici

<400> SEQUENCE: 29

Met Gly Arg Phe Phe Lys Asn Leu Ala Phe Thr Thr Leu Val Leu Val
  1               5                  10                  15

Leu Val Leu Ala Ile Ala Ala Gly Val Gly Ala Ile Val Phe Tyr Asn
             20                  25                  30

Arg Thr Asn Leu Pro Asp Pro Asn Lys Asp Phe Gln Thr Asn Thr Ser
             35                  40                  45

Phe Ile Tyr Phe Asn Asp Ser Lys Thr Lys Leu Gly Ser Leu Ser Val
 50                  55                  60

Gln Asn Arg Gln Thr Ile Gly Tyr Glu Gln Met Pro Lys Ser Ile Lys
 65                  70                  75                  80

Glu Ala Ala Ile Ser Ala Glu Asn Arg Thr Phe Trp Ser Asp Gln Gly
                 85                  90                  95

Ile Ser Ile Gly Gly Ile Val Arg Ala Ala Trp Thr Ile Ala Arg Gly
                100                 105                 110

Gly Glu Met Gln Gly Gly Ser Thr Ile Thr Gln Gln Tyr Ile Lys Ile
                115                 120                 125

Leu Tyr Leu Ser Gln Asp Arg Thr Met Gln Arg Lys Leu Lys Glu Leu
            130                 135                 140

Val Leu Ala Val Lys Met Gly Lys Gln Val Pro Lys Glu Asp Ile Leu
145                 150                 155                 160

Ala Gly Tyr Leu Asn Thr Ile Tyr Phe Gly Arg Gly Ala Tyr Gly Ile
                165                 170                 175

Gln Ala Ala Ala Lys Ser Tyr Phe Asn Val Asp Ala Ser Lys Leu Thr
            180                 185                 190

Val Pro Gln Ser Ala Val Leu Ala Ser Ile Leu Asn Asn Pro Thr Leu
            195                 200                 205

Phe Asp Pro Ser Gly Gly Ala Lys Ala Arg Glu Arg Leu Leu Asn Arg
        210                 215                 220

Tyr Arg Tyr Val Leu Asp Gly Met Leu Glu Ala Gly Asn Ile Thr Gln
225                 230                 235                 240

Ala Glu His Asp Glu Tyr Ser Arg Lys Leu Pro Ala Phe Pro Glu Val
                245                 250                 255
```

-continued

Pro Ile Asn Asn Arg Trp Gly Gly Thr Asn Gly Tyr Leu Leu Lys Met
            260                 265                 270

Val Gln Asn Glu Leu Leu Asp Asp Gly Phe Thr Asp Ser Gln Ile Asn
        275                 280                 285

Gly Gly Gly Leu Lys Val Thr Thr Thr Phe Asp Pro Ala Ala Gln Lys
    290                 295                 300

Ala Ala Val Ala Thr Gly Gln Lys Tyr Lys Lys Leu Ala Gly Ser Asn
305                 310                 315                 320

Ala Gly Lys Asn Gly Ala Lys Asn Leu His Pro Ala Ile Ala Ser Val
            325                 330                 335

Lys Val Gly Thr Gly Glu Val Leu Ala Leu Tyr Gly Gly Asp Asp Tyr
        340                 345                 350

Ile Thr Ser Thr Arg Ser Trp Ala Leu Gln Ala Arg Pro Ala Ala Ser
    355                 360                 365

Thr Phe Lys Thr Tyr Ala Val Ile Ala Gly Met Arg Asn Gly Phe Ser
    370                 375                 380

Leu Lys Ser Lys Leu Asn Gly Asp Thr Phe Thr Pro Gln Gly Asp Ser
385                 390                 395                 400

Val Pro Ile Arg Asn Glu Phe Ser Glu Gln Tyr Gly Asp Val Thr Leu
        405                 410                 415

Gln Lys Ala Thr Glu Asp Ser Ile Asn Thr Ala Phe Val Asp Met Met
            420                 425                 430

Thr Gln Ile Asp Asn Gly Pro Gln Ala Met Leu Lys Ala Ala Asn Asp
        435                 440                 445

Ala Gly Val Pro Lys Gly Ser Gly Trp Asp Leu Asn Asn Arg Met Pro
450                 455                 460

Leu Gly Val Ala Glu Val Ser Pro Leu Asp Gln Ala Thr Gly Tyr Ala
465                 470                 475                 480

Thr Ile Ala Asn Glu Gly Lys Tyr Val Pro Ser His Val Val Ala Lys
            485                 490                 495

Val Thr Asp Ser Ser Gly Lys Thr Leu Tyr Thr Ala Lys Thr Thr Gly
        500                 505                 510

Lys Gln Thr Ile Gln Lys Asp Ile Ala His Asp Thr Thr Tyr Ala Leu
    515                 520                 525

Glu Asn Val Val Asn Glu Gly Thr Gly Ser Ala Val Ser Asn Leu Gly
530                 535                 540

Tyr Pro Val Ala Gly Lys Thr Gly Thr Asn Gly Val Lys Asp Asp Ile
545                 550                 555                 560

Thr Ser Ala Trp Phe Val Ala Tyr Thr Arg Gln Ile Ser Thr Ala Val
            565                 570                 575

Met Tyr Val Ala Gly Asp Gly Asn Glu Asp Leu Asp Pro Tyr Ala
        580                 585                 590

Ala Glu Gly Asp Ser Thr Phe Phe Gly Gly Thr Tyr Pro Ala Arg Thr
    595                 600                 605

Trp Ala Ser Tyr Met Lys Val Ala Met Lys Gly Leu Pro Ser Gln Asp
    610                 615                 620

Phe Pro Lys Pro Asp Lys Val Asn Leu Ser Gly Lys His Tyr Gly Asn
625                 630                 635                 640

Thr Gln Arg Glu Thr Leu Arg Thr Pro Thr Pro Thr Pro Thr Pro Thr
        645                 650                 655

Pro Ser Glu Thr Arg Thr Pro Thr Pro Glu Pro Thr Gln Ser Ser Thr
            660                 665                 670

```
-continued

Pro Ser Arg Pro Glu Pro Thr Gln Thr Ser Ser Glu Pro Glu Pro Thr
        675                 680                 685

Asp Thr Pro Ser Gln Pro Glu Pro Thr Asp Thr Pro Ser Arg Pro Leu
    690                 695                 700

Pro Ser Leu Pro Lys Pro Thr Leu Pro Gly Ile Pro Gly Pro Ser Asp
705                 710                 715                 720

Gly Asp Asp Gly Asp Asn Gly Ala Thr Gly Arg
                725                 730
```

PROPIONIBACTERIAL CELL LINES FOR ORGANIC ACID PRODUCTION

CLAIM OF PRIORITY

This application claims the benefit under 35 USC § 119(e) to U.S. Patent Application Ser. No. 62/686,463, filed on Jun. 18, 2018. The entire contents of the foregoing is hereby incorporated by reference.

TECHNICAL FIELD

The disclosure generally relates to microbial cell lines that overproduce organic acid and methods of making the same.

BACKGROUND

Organic acids refer to carbon-containing compounds having acidic properties. Examples of organic acids include acetic acid, citric acid, gluconic acid, lactic acid, propionic acid, among many others. Because they are fully degradable, organic acids can be used in the production of biodegradable polymers. They also have other important industrial applications, including as food additives.

SUMMARY

The disclosure provides microbial cell lines suitable for industrial-scale production of organic acids and methods of making and isolating such cell lines.

In one aspect, a method of making and isolating a microbial cell line is provided, where the isolated microbial cell line overproduces an organic acid compared to the parental microbial cell line. The method uses serial passage of a parental strain in pH-controlled culture media supplemented with the organic acid, preferably in non-immobilized culture, where the pH is controlled at a value above the pKa value of the organic acid. In some embodiments, the pH is preferably in the range between about 5.5 and about 7.5, more preferably at or near neutral, between about 6.0 and about 7.0, and most preferably at about 7.0. In some embodiments, the culture media is solidified. In some embodiments, the culture medium is supplemented with the organic acid in an amount sufficient to inhibit normal microbial cell growth, e.g., to reduce doubling rate or growth rate, e.g., by at least 5%, 10%, 20%, 30%, 40%, 50%, or more. In some embodiments, the organic acid is supplemented at a progressively increasing amount in successive iterations of the serial passage. In some embodiments, the organic acid is supplemented at the same amount in successive iterations of the serial passage. In some embodiments, the organic acid is propionic acid, lactic acid, acetic acid, or butyric acid. In some embodiments, the organic acid is propionic acid, e.g., the culture media is supplemented with about 1.0%-3.0% of propionic acid, e.g., about 3.0% of propionic acid. In some embodiments, the parental cell line is a wild-type organism. In some embodiments, the parental cell line is a microbial cell line is derived from unicellular microbes.

In another aspect, a microbial cell line that overproduces an organic acid is provided, where the microbial cell line is made and isolated using serial passage in pH-controlled culture media supplemented with the organic acid, where the pH is controlled at a value above the pKa value of the organic acid, preferably in the range between about 5.5 and about 7.5, more preferably at or near neutral, between about 6.0 and about 7.0, and most preferably at about 7.0.

In another aspect, a microbial cell line that overproduces an organic acid is provided, where the microbial cell line has mutations that primarily alter, directly or indirectly, the structure, composition, and/or function of the cellular envelope. Preferably, the microbial cell line includes at least 2 genome mutations identified in Table 3 or analogous mutations. More preferably, the microbial cell line includes all of the genome mutations identified in Table 3 or homologous mutations. In one embodiment, the microbial cell line includes mutations in at least 2 genes identified in Table 3 or analogous mutations thereto. In another embodiment, the microbial cell line includes mutations in all of the genes identified in Table 3 or their homologs (e.g., homologous genes in another species described herein). In another embodiment, the microbial cell line includes a mutation in O-antigen ligase domain-containing protein. In another embodiment, the microbial cell line includes a mutation in M18 family aminopeptidase. In another embodiment, the microbial cell line includes a mutation in amino acid permease. In another embodiment, the microbial cell line includes a mutation in adenine glycosylase.

The microbe can be any microbe that produces an organic acid. In one embodiment, the microbe is from the genus *Propionibacterium* (*Acidipropionibacterium*), and more preferably the species *P. acidipropionici*. In another embodiment, the microbe is from the genus *Lactobacillus*, and more preferably the species *L. acidophilus*. In another embodiment, the microbe is from the genus *Acetobacter*. In another embodiment, the microbe is from the genus *Gluconobacter*. In another embodiment, the microbe is from the genus *Clostridium*, and more preferably the species *C. butyricum*. In some embodiments, the organic acid is propionic acid. In some embodiments, the organic acid is lactic acid. In some embodiments, the organic acid is acetic acid. In some embodiments, the organic acid is butyric acid.

Also provided herein are methods of producing organic acids using the methods and microbes described herein.

DETAILED DESCRIPTION

Figure 1:
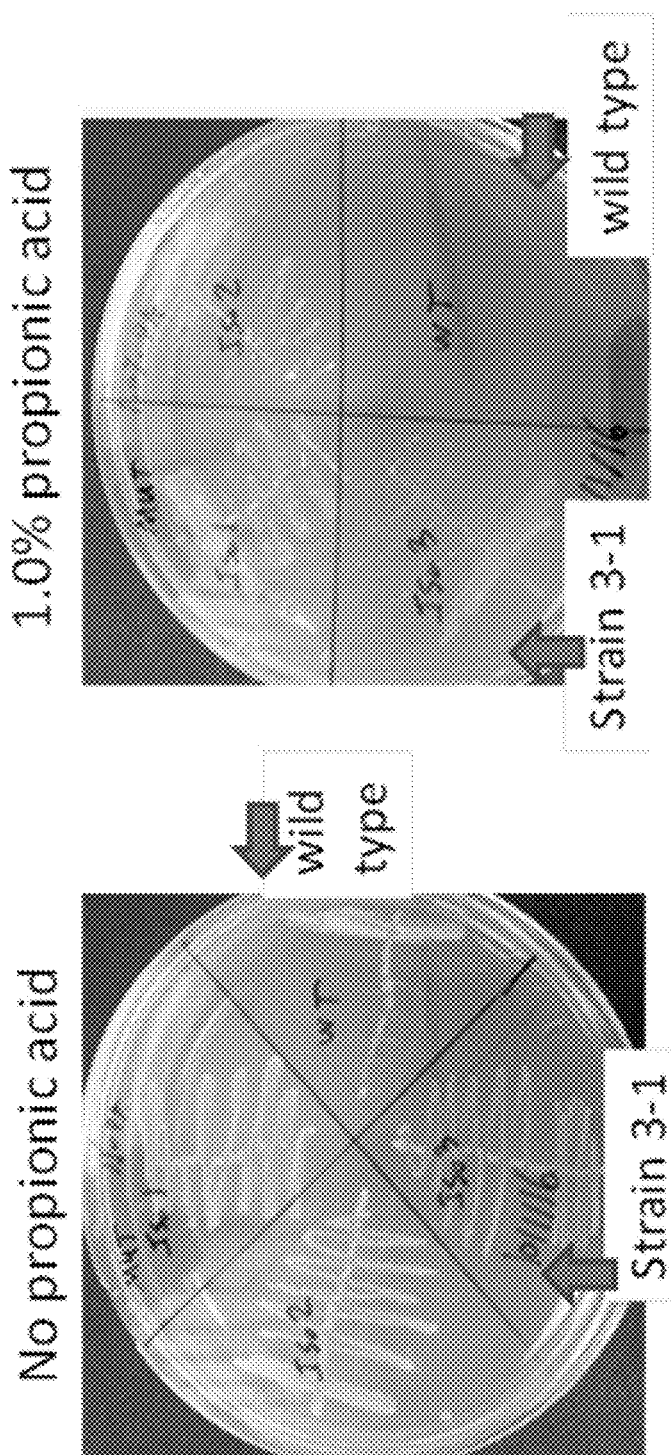
FIG. 1 shows growth of wild-type and mutant *P. acidipropionici* on solid buffered medium with or without addition of 1.0% PA, showing the phenotype of Strain 3-1.

The most common organic acids are carboxylic acids, whose acidity is associated with the carboxyl group (—COOH). They are generally weak acids with pKa values between about 4-5. Propionic acid ("PA"), for example, is a carboxylic acid with the chemical formula $C_2H_5COOH$ or $C_3H_6O_2$. It is a colorless, oily, and pungent (think Swiss cheese and sweat) liquid and has physical properties between those of the smaller carboxylic, formic, and acetic acids, and the larger fatty acids. It has a molecular weight of about 74.1 g/mol, and a pKa of about 4.9, which means in a solution having a pH of about 4.9, half of the PA is in the protonated (or undissociated), uncharged state ($C_2H_5COOH$), while the other half is in the deprotonated (or dissociated), negatively charged state ($C_2H_5COO^-$), known as propionate or propanoate ion, which can form salt or ester compounds. As the pH decreases (becoming more acidic), more PA is in the protonated, uncharged state; when the pH increases (becoming more basic), more PA is in the deprotonated, negatively charged state.

Because PA inhibits the growth of mold and some bacteria at levels between 0.1 and 1% (w/v), PA and its salts are used as a preservative in both animal feed and human food (such as baked goods). In the United States, PA is "generally recognized as safe," or GRAS, by the Food and Drug Administration when used as a food additive. It is also approved for use as a food additive in Australia, New Zealand, and the EU. In addition, PA is an important intermediate in the synthesis of other chemicals, such as cellulose-derived plastics, pesticides, fruit flavors, perfume bases, and pharmaceuticals.

While they are widely distributed in nature, commercial production of organic acids has generally relied on chemical synthesis because it is more economically competitive. For example, PA is currently commercially produced almost exclusively through petrochemical processes. As prices for crude oil and petrochemicals increase, along with the rapid development in the biotechnology field, the economic gap between manufacturing costs of PA via chemical synthesis and via microbial fermentation is narrowing. Coupled with growing concerns about energy shortages and environmental pollution, there has been an increasing interest in commercial-scale biosynthesis of organic acids such as PA from renewable resources.

Microbial production of organic acids by fermentation has been known and used for centuries. For example, *Aspergillus niger* and *Yarrowia lipolytica* have been used to produce citric acid; *Lactobacillus* has been used to produce lactic acid; *Clostridium* has been used to produce acetic acid; *Aspergillus niger* and *Gluconobacter* have been used to produce gluconic acid.

*Propionibacterium* is the microorganism most often used in the production of PA (as well as vitamin $B_{12}$ and Swiss cheese). *Propionibacterium* is a gram-positive, non-motile, non-spore forming, rod-shaped, anaerobic genus of bacteria that includes the species *P. freudenreichii, P. acidifaciens, P. cyclohexanicum, P. australiense, P. acidipropionici, P. jensenii, P. thoenii, P. microaerophilum, P. olivae, P. damnosum, P. propionicum, P. acnes, P. avidum, P. granulosum, P. humerusii,* and *P. lymphophilum*. For industrial PA production, the most commonly used strain is *P. acidipropionici*. (A proposal has been made to reclassify the species within the genus *Propionibacterium* into three novel genera: *Acidipropionibacterium, Cutibacterium,* and *Pseudopropionibacterium* (Scholz & Kilian 2016). However, *Propionibacterium acidipropionci* and *Acidipropionibacterium acidipropionici* are still used somewhat interchangeably.) The optimal pH and temperature for *Propionibacterium* cell growth are about 6.0-7.0 and about 30-37° C., respectively (Ahmadi et al. 2017). Cell growth is inhibited in pH less than about 5.0, although fermenters started at neutral pH can reach pH 4.4 (Rehberger and Glatz 1998). Ahmadi et al. provides an overview of PA production on several carbon sources by various species of *Propionibacterium* as reported in the literature (Ahmadi et al. 2017) and is incorporated herein by reference.

PA can also be produced by other anaerobic bacteria, such as certain species of *Anaerovibrio, Bacteroides, Clostridium, Fusobacterium, Megasphaera, Propionispira, Selenomonas,* and *Veillonella*.

There are a number of fermentation pathways that convert carbon sources to PA through a series of enzymatic reactions. The primary fermentation pathway involved in PA production, especially in propionibacteria, is known as the Wood-Werkman cycle, which produces propionate from pyruvate, the terminal product from glycolysis, and involves many intermediates, including oxaloacetate, malate, fumarate, succinate, succinyl-CoA, methylmalonyl-CoA, and propionyl-CoA, and many enzymes, including oxaloacetate transcarboxylase, biotin-dependent carboxytransferase, CoA transferase, fumarate hydrolase, lactate dehydrogenase, coenzyme $B_{12}$-dependent methylmalonyl-CoA mutase, malate dehydrogenase, and succinate dehydrogenase.

While most pyruvate is converted to PA/propionate during fermentation, some is converted to acetate. The acetate formation pathway involves intermediates acetyl CoA and acetyl phosphate, and enzymes pyruvate dehydrogenase complex, phosphotransacetylase, and acetate kinase.

A number of carbon sources have been used for microbial PA production, including glucose, fructose, maltose, sucrose, xylose, lactose, glycerol, lactate, flour hydrolysate, molasses, whey, and a combination thereof. A number of culture systems such as batch, fed-batch, and continuous fermentation have been used.

However, for commercial-scale microbial production of organic acids to be economically viable, the fermentation process must be able to convert carbon sources at a high yield (amount of organic acid production from carbon source, typically measured in g/g) and high productivity (rate of organic acid production, typically measured in g/L·h).

Various fermentation technologies, including fed-batch, continuous culture, multi-stage, cell immobilization, and extractive fermentation systems, have been explored to increase the yield of organic acid production. However, the modest increase in yield and productivity often comes is offset by a significant increase in production cost.

For example, coculture methods have been used to produce PA using whey as feedstock (WO 85/04901; EP 0141642 A1). WO 85/04901 describes the use of *Lactobacillus casei* subspecies *rhamnosus* in the presence of *Veillonella cricetid* to interconvert lactate to propionate via a two-stage fermentation process. In the first stage, carbohydrates are converted to lactic acid by *L. casei*; in the second stage, lactic acid is fermented to PA by *V. cricetid*. (The genera *Lactobacillus* and *Veillonella* both belong to the phylum Firmicutes, whereas the genus *Propionibacterium* belongs to the phylum Actinobacteria.) EP 0141642 also describes the use of a mixed culture of lactic acid-producing bacteria (*L. casei*) and PA-producing bacteria (*P. shermanii*) to maximize the fermentation yield. The coculture systems of WO 85/04901 and EP 0141642 are reported to be very productive in terms of PA production from lactose, with final yields ranging from 20-100 g/L. However, such coculture systems have considerable implications for process parameters. For example, they suffer from a lack of control over the growth and metabolic activity of each member of the system, which can lead to failure of either member to grow or to contribute to formation of the desired product. A lack of reproducibility is common with coculture systems.

One major problem associated with microbial production of organic acids is the strong inhibitory effect of the end product on cell growth and the fermentation process, leading to low production yield and productivity. Acid tolerance was assumed to be crucial to improving the yield and productivity of PA-producing strains (Rehberger and Glatz 1998). The elevated inhibitory effect of PA at pH 4.5-5.0 as compared to lactic acid was attributed to the fact that at this pH range, about half of PA (which has a pKa of about 4.9) would be present in the undissociated, protonated, and uncharged form, whereas lactic acid (which has a pKa of about 3.1) would mostly be in the dissociated, deprotonated, and charged form. It was assumed that because the undissociated acid could penetrate the cell wall and membrane more easily, more PA than lactic acid could get into the cell and exert its inhibitory effect. Enhancement of acid tolerance was thus thought to be an effective strategy to alleviate end-product inhibition and improve PA production. Accordingly, attempts have been made to create "acid tolerant" mutants of propionibacteria under high PA and either uncontrolled or low pH conditions.

For example, adaptive evolution via serial passage has been used to obtain mutant P. acidipropionici with improved acid tolerance (Woskow and Glatz 1991; Zhu et al. 2010). Serial passage is a method of growing microorganisms such as bacteria in two or more iterations in artificial environments, often created in a laboratory setting, to generate spontaneous mutations in the microorganisms as they evolve over the course of the experiment to adapt to one or more new environmental conditions designed for the experiment. For example, repeatedly subjecting microbes to extreme acidic conditions will lead to spontaneous mutations that allow the microbes to adapt to or tolerate such conditions.

In prior work, to create mutations that confer acid-tolerance, the mutant P. acidipropionici strains were adapted to increasing PA concentrations by repeated and serial transfers in selection media containing increasing amounts of PA (from 0.5% to 5% (Woskow and Glatz 1991) or 1.5 g/L to 20 g/L (Zhu et al. 2010)) over a period of one year or longer. Importantly, in these experiments, pH in the selection media having increasing amounts of PA was not controlled, presumably because it was assumed that the inhibitory effects on cell growth and PA production were caused by the acidity of PA.

P. acidipropionici mutant(s) with enhanced PA production has also been obtained by immobilization and adaptation in a fibrous-bed bioreactor (Suwannakham and Yang 2005; Suwannakham 2005). The ability to obtain acid-tolerant mutant(s) in fibrous-bed bioreactor was attributed to the high cell density and viability maintained in the bioreactor and distinct physiology and survivability of immobilized cells as a result of their direct contact with each other and with a solid surface. The higher PA production was attributed in part to higher activity levels of oxaloacetate transcarboxylase and CoA transferase in the mutant(s). Despite the higher PA yield, in the fibrous-bed bioreactor with high cell density, cell growth is limited. Moreover, fibrous-bed bioreactors are expensive and not scalable, and their uses are limited to small-to-medium scale productions.

More recently, random mutagenesis strategies such as genome shuffling have been used to accelerate directed microbial evolution. For example, Guan et al. reported the use of genome shuffling to generate an acid-tolerant mutant P. acidipropionici strain (Guan et al. 2012). To obtain the strain, four successive rounds of genome shuffling via protoplast fusion were performed, and the acid-tolerant strain was selected using media supplemented with increasing amounts of PA (from 5 to 20 g/L). Again, pH in the selection media having increasing amounts of PA was not controlled, presumably because it was assumed that the inhibitory effects on cell growth and PA production were caused by the acidity of PA.

Subsequent analyses identified 24 proteins that significantly differed between the parental and shuffled strains (Guan et al. 2014). The detected proteins were reported to fall into four broad functional classes: cellular metabolism and energy production; DNA replication, RNA synthesis, and translation; posttranslational modification, protein folding, and chaperones; and hypothetical proteins of unknown function.

In another study, genome shuffling was used to generate acid-tolerant mutant P. acidipropionici, P. intermedium, and P. jensenii strains (WO 2017/055932 A2). Three successive rounds of genome shuffling were performed for each set of strains, each followed by selection of colonies from the acidic (pH 3) side of pH/PA gradient plates prepared using agar culture media supplemented with 5 g/L of PA at either pH 3 or pH 6.5. Final individual recombinants were randomly selected after serial dilutions in culture media plates and screened in a 96 well plate containing 100 µl of culture media at pH 5 and 25 g/L of PA. The mutant strains were reported to have enhanced yields of PA relative to native Propionibacterium and other known derivative strains. Genomic analyses of one of the mutant P. acidipropionici strains identified a number of modified genes, including those encoding the ABC polar amino acid transporter, the Cytochrome C biogenesis protein, the ABC multiple sugar transporter, the large subunit of ribosomal RNA, the long chain acyl-CoA synthetase, and the cation diffusion facilitator. In addition, an extra copy of the whole ribosomal RNA gene and an extra copy of the arginine deiminase regulon (ArgR) with a point mutation were found in the mutant strain.

Targeted metabolic engineering of propionibacteria has also been used to increase PA production. These studies generally target enzymes involved in pyruvate metabolism pathways to, for example, either inhibit the acetate formation pathway or enhance the PA formation pathway. For example, Yang and Suwannakham created engineered P. acidipropionici strains with genes encoding acetate kinase (which catalyzes conversion of acetyl phosphate into acetate) and/or phosphotransacetylase (which catalyzes conversion of acetyl CoA into acetyl phosphate) knocked out, with the goal of eliminating or reducing acetate formation and thereby enhancing PA production (US 2011/0151529 A1; Suwannakham 2005).

Yang et al. created engineered P. acidipropionici and P. freudenreichii subsp. shermanii strains transformed with propionyl-CoA:succinate CoA transferase genes to increase PA production by overexpression propionyl-CoA:succinate CoA transferase, which catalyzes conversion of propionyl CoA into propionate (WO 2012/064883 A2). The resulting strains were reported to have increased PA production and resistance to PA, as well as resistance to acidic pH in general. The increased CoA transferase activity is believed to increase carbon flux through the PA formation pathway over the acetate formation pathway.

The table below describes a list of genes that have been manipulated using recombinant DNA. These genes constitute conventional genetic targets where regulatory mutations might be expected to increase PA yields.

TABLE 1

| Gene(s) | Organism | Effect | Reference |
| --- | --- | --- | --- |
| OtsA (trehalose biosynthesis) | P. acidipropionici | Artificially over-expressed | Jiang et al. 2015 |
| Several genes in arginine deaminase and glutamate decarboxylase systems | P. jensenii | Artificially over-expressed | Guan et al. 2016 |

TABLE 1-continued

| Gene(s) | Organism | Effect | Reference |
| --- | --- | --- | --- |
| Propionyl-CoA:succinate CoA transferase | P. acidipropionici P. shermanii | Artificially over-expressed | Wang et al. 2015 WO 2012/ 064883 A2 |
| Acetate kinase | P. acidipropionici | Artificial knock out | Suwannakham et al. 2006 Suwannakham 2005 US 2011/ 0151529 A1 |
| Phosphotrans-acetylase | P. acidipropionici | Artificial knock out | US 2011/ 0151529 A1 |

Targeted genetic engineering in propionibacteria, however, is challenging. As an initial matter, the effect of acid alteration and stress on bacterial physiology is complex and not well understood, making it difficult to improve tolerance towards organic acids through manipulation of specific genes. Indeed, despite knowledge about the identity of the intermediates and enzymes in the Wood-Werkman pathway that form PA in propionibacteria, genetic manipulations of the genes in this pathway have not increased PA yields to a significant extent.

Moreover, the high GC content in propionibacteria makes it difficult to identify the locations of individual genes and all of the coding regions in the genome, which complicates genetic manipulation. In addition, there are only a small number of cloning vectors available for introducing recombinant DNA into propionibacteria cells, which are known to have low transformation efficiency. Selection of transformants is also complicated by the ability of propionibacteria to quickly develop spontaneous resistance to antibiotic markers.

In addition to these challenges, the use of recombinant DNA for producing microbial cell lines is incompatible with the development of an organic food ingredient such as PA. At least in the United States, PA or other organic acids produced by genetically engineered microbes cannot be labeled as "organic" or "natural preservative," which is especially important in the food industry. Therefore, there remains a need for new microbial strains suitable for industrial-scale production of organic acids and methods of making and isolating such strains.

The toxicity of organic acids towards microbes is not well understood despite its relevance in the food and chemical industries that use fermentation for organic acid production. Despite knowledge about the identity of the intermediates and enzymes in the Wood-Werkman pathway that forms PA in propionibacteria, genetic manipulations of the genes in this pathway have not increased PA yields to a significant extent. One reason could be that these genes do not limit PA formation. Therefore, altering their sequence or expression would not change PA levels. Instead, it is argued here that other cellular targets control PA yields, but their identities could not be predicted based on current knowledge. The unknown process is what limits PA formation. Since this process is not known, the genes involved in this process cannot be predicted.

Prior efforts in creating PA-resistant bacteria through serial passage or genome shuffling have generally used media with increasing amounts of PA but either without pH control or at a pH significantly below the pKa of PA. This is based on the idea that toxicity, and therefore resistance, arises from the concentration of the organic acid. However, this approach does not consider the mechanism of organic acid uptake by the cell that involves the transporter system, which depends on the nature of the transporter and the membrane or envelope in which it is located.

Organic acids are weak acids with pKa values generally between about 4-5. The relationship between pH and pKa is described by the Henderson-Hasselbalch equation:

$$pH = pKa + \log_{10}([A^-]/[HA])$$

wherein [HA] is the concentration of the protonated, undissociated, and uncharged weak acid, and [A$^-$] is the concentration of the deprotonated, dissociated, and negatively charged conjugate base. In a typical fermentation process, the pH of the microbial culture when the organic acid reaches maximum concentration is approximately at the pKa of the organic acid without the use of a buffering agent. A solution having a pH of about 4-5 is not that acidic relative to the known pH tolerance of organic acid producing bacteria. Most of these bacteria do grow at pH values in this range, although the optimum pH for cell growth is typically about 6-7.

Intracellular transport of organic acids can be achieved through diffusion or through the action of membrane transport protein systems depending on whether the organic acids are charged or uncharged. When organic acids are not deprotonated or dissociated, they are uncharged. In this state, they can diffuse across the cellular membranes without reliance on transport systems. Charged molecules, however, always require a transport system to be translocated across membranes.

At a pH value that equals its pKa value, half of the organic acid is in the protonated (or undissociated), uncharged form, while the other half is in the deprotonated (or dissociated), negatively charged form. At pH values below their pKa values, organic acids would mostly be uncharged because their carboxyl groups would be protonated. At pH values above their pKa values, organic acids would mostly be unprotonated or dissociated and therefore negatively charged.

At high concentrations of the organic acid, the pH is relatively low, and the organic acid would mostly be in the uncharged state and could diffuse into the cell in its acid form. This is the basis for prior efforts to isolate organic acid resistant microbes either without pH control or at a pH significantly below the pKa of the organic acid. The approach in theory would generate cell lines with mutations that produced resistance due to diffusion-based organic acid cell entry. It was assumed that the uncharged organic acid would diffuse through the cell membrane into the cytoplasm and release protons due to the relatively alkaline pH inside the cell; the increase in intracellular acidity would inhibit cell growth and organic acid formation. In other words, it was assumed that organic acids in their uncharged state limited their own production. Despite the published literature and patents, in our experience, this approach does not generate resistant microbes effectively, and may require years of passage to work.

We hypothesized that it was not the acidity of the organic acid that was toxic, as previously assumed by others. Rather, it was the deprotonated, negatively charged form or the neutral salt of the organic acid (propionate) that was toxic, and would be more effective as a selection agent to recover spontaneous resistance mutations.

Unlike prior efforts, we hypothesized that the use of pH control at a value above the pKa value of the organic acids to be produced, and preferable at least 1 unit above, would ensure that most of the organic acids remain in a charged and deprotonated form. In this form, they would remain dependent on protein transport systems for intracellular uptake.

This would avoid recovery of cell lines with mutations that produced resistance due to diffusion-based organic acid cell entry, if such mutations could be discovered.

Specifically, the process used was serial passage of the starting microbial cell line (usually but not necessarily a wild-type) in free-cell (i.e. non-immobilized or planktonic) culture in a bacteriologic culture medium supplemented with organic acid of interest in an amount that is sufficient to inhibit normal microbial growth (either in progressively increasing amounts or the same amount for all passages) under conditions of continued pH control at a specific pH that is above the pKa value of the organic acid. The pH is controlled at a value above the pKa value of the organic acid, preferably in the range between about 5.5 and about 7.5, more preferably at or near neutral, between about 6.0 and about 7.0, and most preferably at about 7.0. Although the present examples describe the use of *Propionibacterium*, other microbes can be used that are fermentative organisms that excrete organic acids, e.g., *Lactobacillus, Acetobacter, Gluconobacter*, or *Clostridium*. The organic acid used can be, e.g., PA, lactic acid, acetic acid, or butyric acid. In some embodiments, the microbe is from the genus *Propionibacterium (Acidipropionibacterium)*, and more preferably the species *P. acidipropionici*, and the organic acid is PA. In some embodiments, the microbe is from the genus *Lactobacillus*, and more preferably the species *L. acidophilus*, and the organic acid is lactic acid. In some embodiments, the microbe is from the genus *Acetobacter* or the genus *Gluconobacter*, and the organic acid is acetic acid. In some embodiments, the microbe is from the genus *Clostridium*, and more preferably the species *C. butyricum*, and the organic acid is butyric acid.

Using our method of serial passage with pH control, we were able to create and isolate a new microbial strain having increased organic acid production compared to the parental strain in less than two weeks, much faster than using the conventional serial passage method described in Woskow and Glatz 1991, which generally takes at least one year. Our method is also much less complex and more easily scalable than other random mutagenesis methods such as genome shuffling and cell immobilization in a fibrous-bed bioreactor or targeted genetic engineering. Organic acids produced by mutant cell lines created and isolated using serial passage with pH control can be labeled as "organic" or "natural preservative," which is especially important in the food industry.

The same method of serial passage with pH control can be used to make and isolate a variety of microbes, including but not limited to propionibacteria, lactobacilli, acetic acid bacteria, and clostridia, that overproduce a number of organic acids, including but not limited to PA, lactic acid, acetic acid, and butyric acid. All charged molecules depend on transport systems and their associated membranes/envelopes for function. Alterations in these cellular components would achieve the same outcome as described here for propionate for other organic acids.

The same selection method (i.e., using bacteriologic culture medium supplemented with organic acid of interest in an amount that is sufficient to inhibit normal microbial growth under conditions of continued pH control at a pH that is above the pKa value of the organic acid) can be used in screening microbial libraries generated from genome shuffling or other random mutagenesis methods for isolates that exhibit increased organic acid tolerance and production.

Using this pH control method, we were able to target unique mechanisms for resistance that depended on transport and/or unpredictable intracellular targets including those involved in regulation and metabolism. Genome resequencing was then used to identify the critical genes through their mutational changes that caused the genetic resistance to high concentrations of organic acids.

The resulting mutations generally affected cellular envelope functions, as shown in Table 2.

TABLE 2

ENVELOPE AND ASSOCIATED CATEGORIES

ENVELOPE FUNCTIONS:

Transporters/membrane proteins (10 affected ORFS): Major facilitator superfamily proteins, amino acid permeases, hypothetical membrane protein, LemA membrane protein, intramembrane metalloprotease, AAA ATPase, sodium-proton antiporter
Gain-of-function in penicillin-binding protein and amino acid permease
Cell wall/peptidoglycan synthesis: Penicillin-binding proteins, O-antigen ligase domain-containing proteins (many mutations)
ENVELOPE MODIFYING FUNCTIONS:

Oxidation/reduction: Flavin reductase, alpha/beta hydrolase, pyruvate carboxylase, MocA oxidoreductase, protophyringen oxidase, KGD
Glycosyl transferases/hydrolases: Glycosyl transferase, glycosyl hydrolase, adenine glycosylase These mutations primarily altered the structure and composition and function of the cellular envelope, which consists of the cell wall and membrane(s), including the cytoplasmic membrane. A complete list of the mutations identified is provided in Table 3. We did not see any mutations in genes that have been targeted for metabolic engineering and manipulated using recombinant DNA as previously reported (see Table 1). Mutations in multiple genes appear to be required to produce the mutant phenotype (such as increased growth in media supplemented with organic acid and/or overproduction of organic acid compared to the starting microbial cell line). This is in direct contrast to prior knowledge where single genes were manipulated to try to change PA yields.

In accordance with the present invention, other conventional microbiology, molecular biology, recombinant DNA, and biochemical techniques may be used. Such techniques are fully explained in the literature and within the skill of the art. The invention will be further described in the following examples, which do not limit the scope of the methods and compositions of matter recited in the claims.

EXAMPLES

Example 1

Isolation of Strain 3-1

A *P. acidipropionici* (ATCC 25562) was grown to high cell density in 10 mL M24+2.0% glucose media. Serial dilutions of this culture ($10^0$ to $10^{-3}$) were then plated on solid M24+2.0% glucose media, solidified with agar, supplemented with 1.0%, 2.0%, and 3.0% (w/v) PA, all neutralized to pH 7.0 using sodium hydroxide. Cells were also plated on solid M24+2.0% glucose media with no additional PA.

After a 5-day anaerobic incubation at 30° C., colony growth at the different PA concentrations was assessed. Three colonies grew on the 3% PA plate plated with undiluted cells; no colony grew on the 3% PA plates plated with diluted cells. The three colonies were isolated and re-streaked onto no-PA, 2.0% PA, and 3.0% PA plates (all neutralized to pH 7.0 using sodium hydroxide), along with freshly grown wild-type *P. acidipropionici* cells.

After a second 5-day anaerobic incubation at 30° C., colony growth at the different PA concentrations was again assessed. All three isolates, but not wild-type, were able to grow on the 1.0% PA plate (FIG. 1). Only isolate #1 was able to grow on the 2.0% PA and 3.0% PA plates. This isolate was named strain 3-1 ("3" denotes 3.0% PA, and "1" denotes isolate #1). Isolate #1 was inoculated into 5 mL liquid M24+2.0% glucose media and grown to high cell density, and frozen permanents of these cells were made.

After the phenotype of resistance to 3.0% PA on solid media was confirmed for strain 3-1, PA production in 10 mL batch cultures and 1 L bioreactor cultures of this strain was compared to its parental *P. acidipropionici* (ATCC 25562) cells by HPLC in a broad range of media and cultivation conditions.

Strain 3-1 was deposited under the name NFS-2018 on Jul. 10, 2019, in the American Type Culture Collection (10801 University Blvd. Manassas, Va. 20110-2209) and assigned Accession Number ATCC PTA-125895).

Example 2

PA Production by Strain 3-1 and Wild-Type *P. acidipropionici*

Wild type *P. acidipropionici* (ATCC 255562) and strain 3-1 were cultivated from a frozen permanent at 30° C. under anaerobic condition in M24 medium supplemented with 2% glucose. The cells were sub-cultured every 48 hr into fresh M24 medium starting at 10 mL then at 50 mL to use as seed for the 1 L bioreactor vessels.

For preparation of wheat flour medium, 75 g of American cake flour was added to 1 L of ddH2O in a sterile 2 L flask while mixing. One mL of Enzenco alpha-amylase and 500 mL of 50 ppm of $CaCl_2$ was added to the mixture to hydrolyze the cake flour. The pH was adjusted to 6.0 by adding 5 mL of 5M NaOH and the temperature was held at 90° C. for 1 hour. The mixture was allowed to cool then incubated at 37° C. overnight. After the overnight incubation, the temperature was raised to 60° C. and pH adjusted to 7.0 by adding 2 mL of 5M NaOH. To release glucose, 1 mL of Enzenco glucoamylase, 0.05 g of protease, 0.4 g of MgSO4, and 10 g of Ohly KAT yeast extract were added to the mixture while stirring. The mixture was held at 60° C. for 2 hours. The mixture was allowed to cool then added to a glass-jacketed bioreactor vessel then sealed. Before autoclaving, the pH was calibrated.

Figure 2:
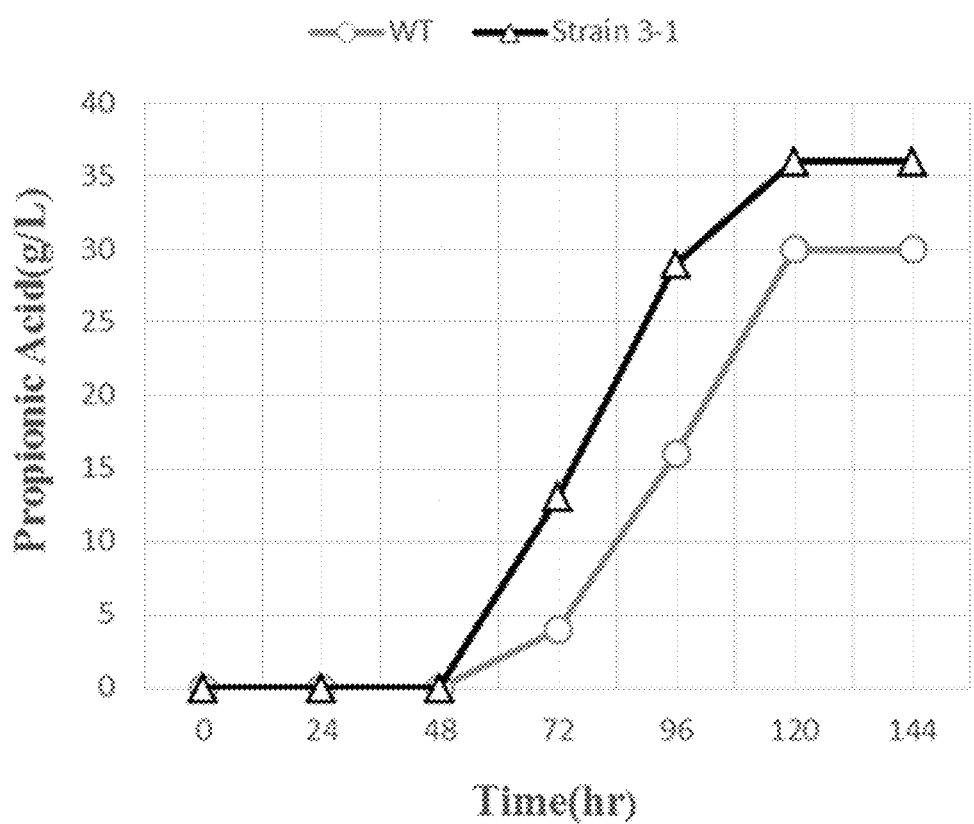
FIG. 2 shows production of PA by a mutant strain of *P. acidipropionici* (Strain 3-1) relative to wild-type in bioreactors using bleached American Beauty Cake Flour (WFM as bolus). 1:200 inoculation, 1 L working culture, 5% (w/v) glucose equivalent WFM, 30° C., pH 7 (NaOH, 5M).

Fermentations were performed at 1 L volumes in the 3 L bioreactor vessels. The temperature was maintained at 30° C., the pH was maintained at 7.0 using 5M NaOH, and cultures were agitated at 200 rpm. 3 mL of filtered sterile trace element solution was added to the bioreactor before inoculation. The glucose concentration was determined using a YSI 2900 analyzer. The 1 L of wheat flour medium was seeded with 5% inoculum. Samples were removed every 24 hours for PA analysis on the HPLC. The results are shown in FIG. 2.

Both strain 3-1 and the parental wild-type strain reached maximum PA concentration at about 120 hours. The maximum concentration of PA produced by strain 3-1 is about 36 g/L, compared to about 30 g/L by the parental wild-type strain.

Additional experiments were carried out under 5-6 different conditions, 3-4 times each, to compare PA production by strain 3-1 and wild-type *P. acidipropionici*. Results similar to those shown in FIG. 2 were obtained. There is a minimum of 15% increase in PA production by strain 3-1 compared to the wild-type after 60 hours of culturing.

Example 3

Genomic Analyses of Strain 3-1

Genome resequencing of strain 3-1 was used to identify the critical genes through their mutational changes that caused the genetic resistance to high concentrations of organic acids.

65 loss of function mutations in 29 genes were identified. The mutations generally affected cellular envelope functions, as shown in Table 2. These mutations primarily alter the structure and composition and function of the cellular envelope, which consists of the cell wall and membrane(s), including the cytoplasmic membrane. A complete list of the mutations identified in strain 3-1 is provided in Table 3.

TABLE 3

STRAIN 3-1 GENOME MUTATIONS

| Coordinates | ORF | SEQ ID NO. | Change |
|---|---|---|---|
| Non-synonymous | | | |
| 130744-130746 | ASQ49_RS00690 class I SAM-dependent methyltransferase | 1 | Arg → His |
| 130744-130746 | ASQ49_RS00695 MFS transporter | 2 | Thr → Pro |
| 130748 | ASQ49_RS00690 class I SAM-dependent methyltransferase | 1 | Pro → Leu |
| 130752 | ASQ49_RS00695 MFS transporter | 2 | Arg → Gly |
| 181601 (80% confidence) | ASQ49_RS00915 LemA family protein | 3 | Insertion (no frameshift) |
| 181607-181609 | ASQ49_RS00915 LemA family protein | 3 | Gln → Leu |
| 240311 | ASQ49_01155 Flavin reductase | 4 | Pro → His |
| 240440 | ASQ49_01155 Flavin reductase | 4 | Ala → Val |
| 281222 | ASQ49_RS01330 Hypothetical protein (BLAST hit to MFS transporter) | 5 | Trp → STOP |
| 344598 | ASQ49_RS01635 MFS transporter | 6 | Thr → Pro |
| 525954 | ASQ49_RS02385 glycosyl transferase family 1 | 7 | Ala → Glu |
| 548143-548147 | ASQ49_RS02475 Hypothetical protein (Strong BLAST hits to O-antigen ligase and membrane protein) | 8 | Ala → Gly Gly → Leu |
| 548153-548156 | ASQ49_RS02475 Hypothetical protein (Strong BLAST hits to O-antigen ligase and membrane protein) | 8 | Ala → Val Gly → Leu |
| 548162 | ASQ49_RS02475 Hypothetical protein (Strong BLAST hits to O-antigen ligase and membrane protein) | 8 | Ala → Val |
| 558158-558160 | ASQ49_RS02520 O-antigen ligase domain-containing protein | 9 | His → Gly |
| 558181 | ASQ49_RS02520 O-antigen ligase domain-containing protein | 9 | Gln → His |

TABLE 3-continued

STRAIN 3-1 GENOME MUTATIONS

| Coordinates | ORF | SEQ ID NO. | Change |
|---|---|---|---|
| 558228 | ASQ49_RS02520 O-antigen ligase domain-containing protein | 9 | Ala → Thr |
| 558252 | ASQ49_RS02520 O-antigen ligase domain-containing protein | 9 | Ser → Pro |
| 558258 | ASQ49_RS02520 O-antigen ligase domain-containing protein | 9 | Ser → Pro |
| 558266 | ASQ49_RS02520 O-antigen ligase domain-containing protein | 9 | Arg → Leu |
| 558273 | ASQ49_RS02520 O-antigen ligase domain-containing protein | 9 | Ser → Ala |
| 558279 | ASQ49_RS02520 O-antigen ligase domain-containing protein | 9 | Gln → Glu |
| 558282 | ASQ49_RS02520 O-antigen ligase domain-containing protein | 9 | Glu → Gln |
| 558288-588290 | ASQ49_RS02520 O-antigen ligase domain-containing protein | 9 | Leu → Pro |
| 558291-558293 | ASQ49_RS02520 O-antigen ligase domain-containing protein | 9 | Glu → Val |
| 558306 | ASQ49_RS02520 O-antigen ligase domain-containing protein | 9 | Pro → Ala |
| 558308-558310 | ASQ49_RS02520 O-antigen ligase domain-containing protein | 9 | Thr → Ser |
| 562835 | ASQ49_RS02535 O-antigen ligase domain-containing protein | 10 | Val → Leu |
| 562840 | ASQ49_RS02535 O-antigen ligase domain-containing protein | 10 | Ala → Val |
| 562843 | ASQ49_RS02535 O-antigen ligase domain-containing protein | 10 | Gly → Ala |
| 566353 (*50% frequency) | ASQ49_RS02550 penicillin-binding protein | 11 | Lys → Gln |
| 566356 (*50% frequency) | ASQ49_RS02550 penicillin-binding protein | 11 | Ala → Ser |
| 618017-618019 | ASQ49_RS02820 Phosphotransferase | 12 | Glu → Ala |
| 738302 | ASQ49_RS03340 Alpha/beta hydrolase | 13 | Thr → Ala |
| 742073 | ASQ49_RS03360 Hypothetical protein (BLAST hits to intramembrane metalloprotease) | 14 | Ile → Leu |
| 1176596 | ASQ49_RS05220 gfo/Idh/MocA family oxidoreductase | 15 | Ala → Val |
| 1279986 | ASQ49_RS05630 Alpha/beta hydrolase | 16 | Ile → Val |
| 1331356 | ASQ49_RS05840 Amino acid permease | 17 | Gly → Ser |
| 1331366 | ASQ49_RS05840 Amino acid permease | 17 | Arg → His |
| 1521847 | ASQ49_RS06625 Hypothetical protein (BLAST hits to protoporphyrinogen oxidase) | 18 | Thr → Ala |
| 1816621 | ASQ49_RS07985 Adenine glycosylase | 19 | Ser → Ala |
| 1816687 | ASQ49_RS07985 Adenine glycosylase | 19 | In-frame insertion (1 amino acid) |

TABLE 3-continued

STRAIN 3-1 GENOME MUTATIONS

| Coordinates | ORF | SEQ ID NO. | Change |
|---|---|---|---|
| 1817191 | ASQ49_RS07985 Adenine glycosylase | 19 | Gly → Glu |
| 1817202 | ASQ49_RS07985 Adenine glycosylase | 19 | Glu → Ala |
| 1854503 | SQ49_RS08150 Hypothetical protein (BLAST hit to sodium-proton antiporter) | 20 | Lys → Arg |
| 1854520 | SQ49_RS08150 Hypothetical protein (BLAST hit to sodium-proton antiporter) | 20 | Ile → Met |
| 2679601 | ASQ49_12020 multifunctional oxoglutarate decarboxylase/oxoglutarate dehydrogenase thiamine pyrophosphate- binding subunit/dihydrolipoyllysine-residue succinyltransferase subunit (kgd) | 21 | His → Asp |
| 2927020 | ASQ49_RS13125 Amino acid permease | 22 | In-frame insertion (4 amino acids) |
| 2927030 | ASQ49_RS13125 Amino acid permease | 22 | Gly-Ser → Ala-Ala |
| 2928883 | ASQ49_RS13130 Hypothetical protein (glycosyl gydrolase family) | 23 | Asn → Tyr |
| 3517645 (*50% frequency) | ASQ49_RS15965 M18 family aminopeptidase | 24 | Thr → Arg |
| 3517646 (*50% frequency) | ASQ49_RS15965 M18 family aminopeptidase | 24 | Thr → Ser |
| 3517648 (*50% frequency) | ASQ49_RS15965 M18 family aminopeptidase | 24 | Ser → Thr |
| 3517649 (*50% frequency) | ASQ49_RS15965 M18 family aminopeptidase | 24 | Ser → Gly |
| 3517652 | ASQ49_RS15965 M18 family aminopeptidase | 24 | Ser → Tyr |
| 3517655 | ASQ49_RS15965 M18 family aminopeptidase | 24 | Ser → Asn |
| FRAMESHIFTS | | | |
| 558244 | ASQ49_RS02520 O-antigen ligase domain-containing protein | 9 | |
| 558246 | ASQ49_RS02520 O-antigen ligase domain-containing protein | 9 | |
| 2867178 | ASQ49_RS12835 AAA ATPase | 25 | |
| FRAMESHIFT REPAIRS | | | |
| 448285 | ASQ49_RS02075 DUF1116 domain-containing protein | 26 | |
| 561527 | ASQ49_RS02530 Glycosyl transferase | 27 | |
| 900222 | ASQ49_RS03980 acetyl-CoA carboxylase biotin carboxyl carrier protein subunit | 28 | |
| 919056 | ASQ49_RS04070 Penicillin-binding protein | 29 | |
| 1330401 | ASQ49_RS05840 Amino acid permease | 17 | |
| 1330407 | ASQ49_RS05840 Amino acid permease | 17 | |

Mutations in these genes (or their homologues in other species described herein) likely confer genetic resistance to high concentrations of organic acids by altering the membrane transport protein systems and/or previously unknown intracellular targets involved in regulation and/or metabolism.

Multiple mutations in the same gene imply that the gene is very important for the trait and required multiple changes to contribute to the trait. Noticeably, several genes had three or more mutations, which may indicate their critical roles in limiting organic acid formation. They include genes encoding: O-antigen ligase domain-containing protein (15 mutations in ASQ49_RS02520; 3 mutations in ASQ49_RS02535; and 3 mutations in ASQ49_RS02475 (hypothetical protein with strong BLAST hits to O-antigen ligase and membrane protein)); M18 family aminopeptidase (6 mutations in ASQ49_RS15965); amino acid permease (4 mutations in ASQ49_RS05840); and adenine glycosylase (4 mutations in ASQ49_RS07985).

REFERENCES

1. Woskow S. A., B. A. Glatz. 1991. Propionic acid production by a propionic acid-tolerant strain of *Propionibacterium acidipropionici* in batch and semicontinuous fermentation. Applied and Environmental Microbiology 57:2821-2828.
2. Zhu Y., J. Li, M. Tan, L. Liu, L. Jiang, J. Sun, P. Lee, G. Du, J. Chen. 2010. Optimization and scale-up of propionic acid production by propionic acid-tolerant *Propionibacterium acidipropionici* with glycerol as the carbon source. Bioresource Technology 101:8902-8906.
3. Wang Z., S.-T. Yang. 2013. Propionic acid production in glycerol/glucose co-fermentation by *Propionibacterium freudenreichii* subsp. *shermanii*. Bioresource Technology 137:116-123.
4. Zhuge X., L. Liu, H.-d. Shin, J. Li, G. Du, J. Chen. 2014. Improved propionic acid production from glycerol with metabolically engineered *Propionibacterium jensenii* by integrating fed-batch culture with a pH-shift control strategy. Bioresource Technology 152:519-525.
5. Zhuge X., J. Li, H.-d. Shin, L. Liu, G. Du, J. Chen. 2015. Improved propionic acid production with metabolically engineered *Propionibacterium jensenii* by an oxidoreduction potential-shift control strategy. Bioresource Technology 175:606-612.
6. Coral J. 2008. Propionic acid production by *Propionibacterium* sp. using low-cost carbon sources in submerged fermentation. Dissertation. Federal University of Parana.
7. Zhang A., J. Sun, Z. Wang, S.-T. Yang, H. Zhou. 2015. Effects of carbon dioxide on cell growth and propionic acid production from glycerol and glucose by *Propionibacterium acidipropionici*. Bioresource Technology 175:374-381.
8. Wang Z., M. Lin, L. Wang, E. M. Ammar, S.-T. Yang. 2015. Metabolic engineering of *Propionibacterium freudenreichii* subsp. *shermanii* for enhanced propionic acid fermentation: Effects of overexpressing three biotin-dependent carboxylases. Process Biochemistry 50:194-204.
9. Suwannakham S., Y. Huang, S.-T. Yang. 2006. Construction and characterization of ack knock-out mutants of *Propionibacterium acidipropionici* for enhanced propionic acid fermentation. Biotechnology and Bioengineering 94:383-95.
10. Suwannakham S., S.-T. Yang. 2005. Enhanced propionic acid fermentation by *Propionibacterium acidipropionici* mutant obtained by adaptation in a fibrous-bed bioreactor. Biotechnology and Bioengineering 91:325-337.
11. Suwannakham S. 2005. Metabolic engineering for enhanced propionic acid fermentation by *Propionibacterium acidipropionici*. Dissertation. Ohio State University.
12. Tufvesson P., A. Ekman, R. R. R. Sardari, K. Engdahl, L. Tufvesson. 2013. Economic and environmental assessment of propionic acid production by fermentation using different renewable raw materials. Bioresource Technology 149:556-564.
13. Thierry A., S.-M. Deutsch, H. Falentin, M. Dalmasso, F. J. Cousin, G. Jan. 2011. New insights into physiology and metabolism of *Propionibacterium freudenreichii*. International Journal of Food Microbiology 149:19-27.
14. Scholz C. F. P., M. Kilian. 2016. The natural history of cutaneous propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov. International Journal of Systematic and Evolutionary Microbiology 66:4422-4432.
15. Rehberger J. L., B. A. Glatz. 1998. Response of cultures of *Propionibacterium* to acid and low pH: tolerance and inhibition. Journal of Food Production 61:211-216.
16. Ahmadi N., K. Khosravi-Darani, A. M. Mortazavian. 2017. An overview of biotechnological production of propionic acid: From upstream to downstream processes. Electronic Journal of Biotechnology 28:67-75.
17. Guan N., L. Liu, X. Zhug, Q. Xu, J. Li, G. Du, J. Chen. 2012. Genome-shuffling improves acid tolerance of *Propionibacterium acidipropionici* and propionic acid production. Advances in Chemistry Research 15:143-152.
18. Guan N., H. Shin, R. R. Chen, J. Li, L. Liu, G. Du, J. Chen. 2014. Understanding of how *Propionibacterium acidipropionici* respond to propionic acid stress at the level of proteomics. Scientific Reports 4:6951.
19. Guan N., H. D. Shin, G. Du, J. Chen, L. Liu. 2016. Metabolic engineering of acid resistance elements to improve acid resistance and propionic acid production of *Propionibacterium jensenii*. Biotechnology and Bioengineering 113:1294-304.
20. Jiang L., H. Cui, L. Zhu, Y. Hu, X. Xu, S. Li, H. Huang. 2015. Enhanced propionic acid production from whey lactose with immobilized *Propionibacterium acidipropionici* and the role of trehalose synthesis in acid tolerance. Green Chemistry 15:250-259.
21. EP 0141642
22. WO 85/04901
23. US 2011/0151529 A1
24. WO 2012/064883 A2
25. WO 2017/055932 A2

The invention claimed is:

1. A *Propionibacterium acidipropionici* (*P. acidipropionici*) cell line produced by a method comprising:
  culturing by serial passage in non-immobilized culture a parental *P. acidipropionici* cell line in a culture medium supplemented with an organic acid, wherein the organic acid is propionic acid, lactic acid, acetic acid, or butyric acid, in an amount sufficient to inhibit normal microbial cell growth, wherein the pH of the culture medium is controlled at a value above the pKa value of the organic acid, and
  isolating a *P. acidipropionici* cell line that overproduces the organic acid compared to the parental *P. acidipropionici* cell line, wherein the isolated cell line comprises one or more of the loss of function mutations in genes encoding DUF1116 domain-containing protein (A5Q49_R502075; SEQ ID NO:26) and M18 family aminopeptidase (A5Q49_RS15965; SEQ ID NO:24) identified in Table 3.

2. The *P. acidipropionici* cell line of claim 1, wherein the microbial cell line further comprises one or more additional mutations identified in Table 3.

3. The *P. acidipropionici* cell line of claim 1, wherein the microbial cell line has loss of function mutations in all of the genes encoding the proteins identified in Table 3.

4. A *P. acidipropionici* cell line having at least one loss of function mutation in genes encoding proteins selected from the group consisting of O-antigen ligase domain-containing protein (ASQ49_RS02520; SEQ ID NO:9), amino acid permease (ASQ49_RS13125; SEQ ID NO:17), DUF1116 domain-containing protein (A5Q49_R502075; SEQ ID NO:26) and M18 family aminopeptidase (A5Q49_RS15965; SEQ ID NO:24), and adenine glycosylase (ASQ49_RS07985; SEQ ID NO:19) wherein said *P. acidipropionici* cell line overproduces an organic acid compared to the parental *P. acidipropionici* cell line, and said organic acid is propionic acid, lactic acid, acetic acid, or butyric acid.

5. The *P. acidipropionici* cell line of claim 4, wherein the at least one loss of function mutation is in the gene encoding O-antigen ligase domain-containing protein (ASQ49_RS02520; SEQ ID NO:9).

6. A *P. acidipropionici* cell line deposited in the American Type Culture Collection under Accession Number ATCC PTA-125895.

7. The *P. acidipropionici* cell line of claim 1, wherein the culture media is solidified.

8. The *P. acidipropionici* cell line of claim 1, wherein the organic acid is supplemented at a progressively increasing amount in successive iterations of the serial passage.

9. The *P. acidipropionici* cell line of claim 1, wherein the organic acid is supplemented at the same amount in successive iterations of the serial passage.

10. The *P. acidipropionici* cell line of claim 1, wherein the pH of the media is controlled at a value within the range of about 5.5-7.5.

11. The *P. acidipropionici* cell line of claim 10, wherein the pH of the media is controlled at a value within the range of about 6.0-7.0.

12. The *P. acidipropionici* cell line of claim 11, wherein the pH of the media is controlled at about 7.0.

13. The *P. acidipropionici* cell line of claim 1, wherein the parental cell line is wild-type.

14. The *P. acidipropionici* cell line of claim 1, wherein the microbial cell line is derived from unicellular microbes.

15. The *P. acidipropionici* cell line of claim 1, wherein the organic acid is propionic acid, and the culture media is supplemented with about 1.0%-3.0% of propionic acid.

16. The *P. acidipropionici* cell line of claim 15, wherein the culture media is supplemented with about 3.0% of propionic acid.

* * * * *